United States Patent [19]
Meyer et al.

[11] Patent Number: 5,613,951
[45] Date of Patent: Mar. 25, 1997

[54] SINGLE USE INJECTION DEVICE

[75] Inventors: Philippe Meyer, Zürich, Switzerland; Ewald Pickhard, Vienna, Austria

[73] Assignee: Pharmaplan GmbH, Bad Homburg V.D.H., Germany

[21] Appl. No.: 335,843

[22] PCT Filed: May 19, 1993

[86] PCT No.: PCT/AT93/00085
§ 371 Date: Jan. 9, 1995
§ 102(e) Date: Jan. 9, 1995

[87] PCT Pub. No.: WO93/23099
PCT Pub. Date: Nov. 25, 1993

[30] Foreign Application Priority Data

May 19, 1992 [AT] Austria ................................. 1029/92

[51] Int. Cl.$^6$ ................................................. A61M 5/00
[52] U.S. Cl. ................................... 604/110; 604/218
[58] Field of Search ................................. 604/110, 218, 604/272

[56] References Cited

FOREIGN PATENT DOCUMENTS 9204064  3/1992  WIPO .

*Primary Examiner*—Corrine M. McDermott
*Attorney, Agent, or Firm*—Panitch Schwarze Jacobs & Nadel, P.C.

[57] ABSTRACT

The invention is a single use injection device (1) having an injection cylinder (2) for receiving a liquid medium, an injection needle (6), and a piston (4) which can slide inside the injection cylinder (2) and which is movably linked to a piston rod (5) which extends in the opposite direction to the injection needle (6). An anti-reuse device (7) which is actuated by the medium moved by the piston (4) is arranged in an inlet area (37) of the injection cylinder (2) that faces the injection needle (6) and has a switching member (22) with a sealing section (48) having a larger cross-sectional surface than the cross-section of an opening (33) provided in a retaining member (21) and whose sealing section (48) is retained in a rest position with a circular ring-shaped retaining member (21) which is elastically deformable in the radial direction on the side of the retaining member (21) that faces the piston (4). In the locking position of the switching member (22), the sealing section (48) is located on the side of the retaining member (21) that faces the injection needle (6). A reception room for the switching member (22) or for its sealing section (48) is arranged between the retaining member (21) and the injection needle (6). The switching member (22) has a guiding element (23) adjacent to the sealing section (48) which is guided in a guiding path (49).

36 Claims, 14 Drawing Sheets

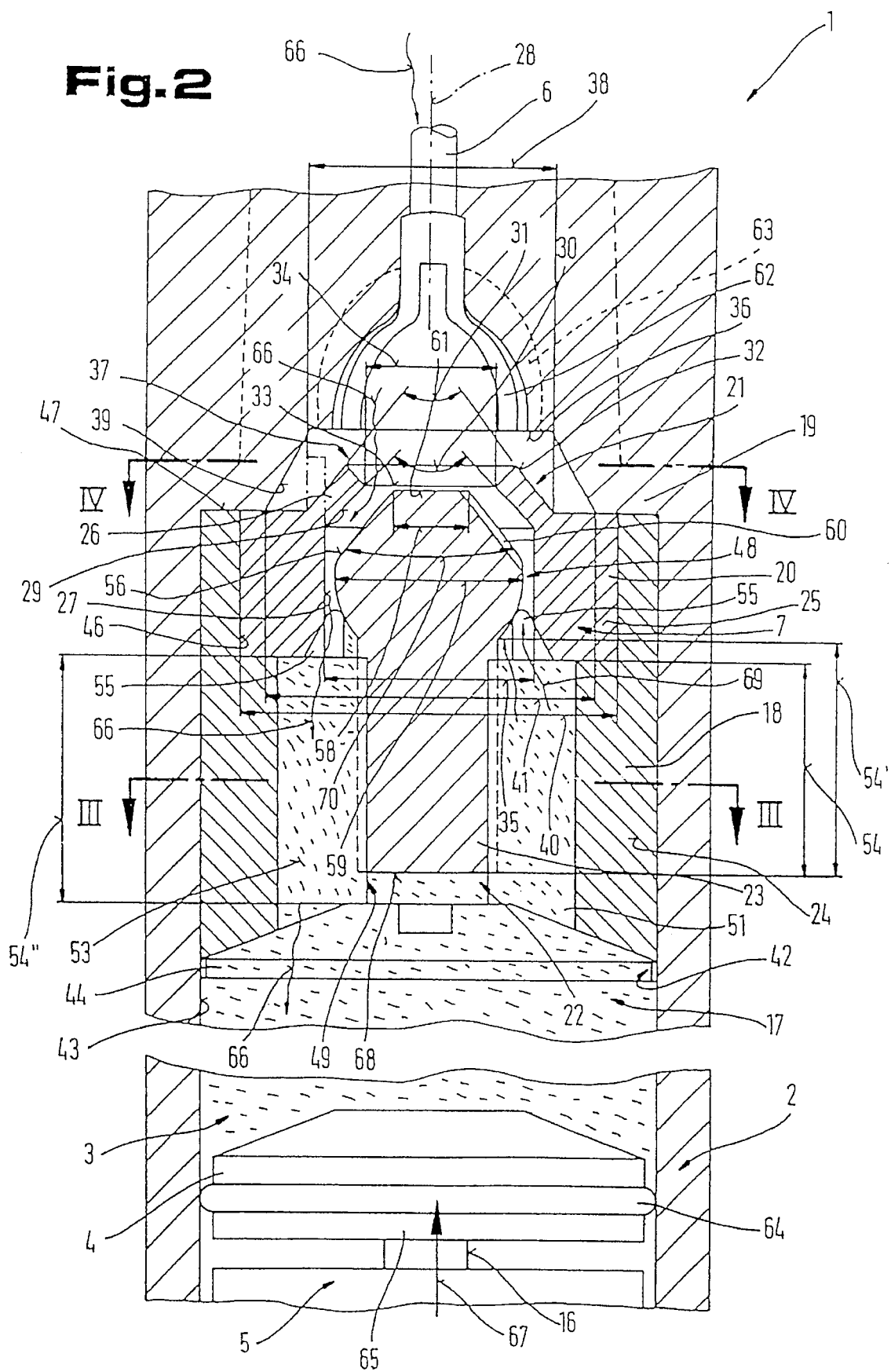

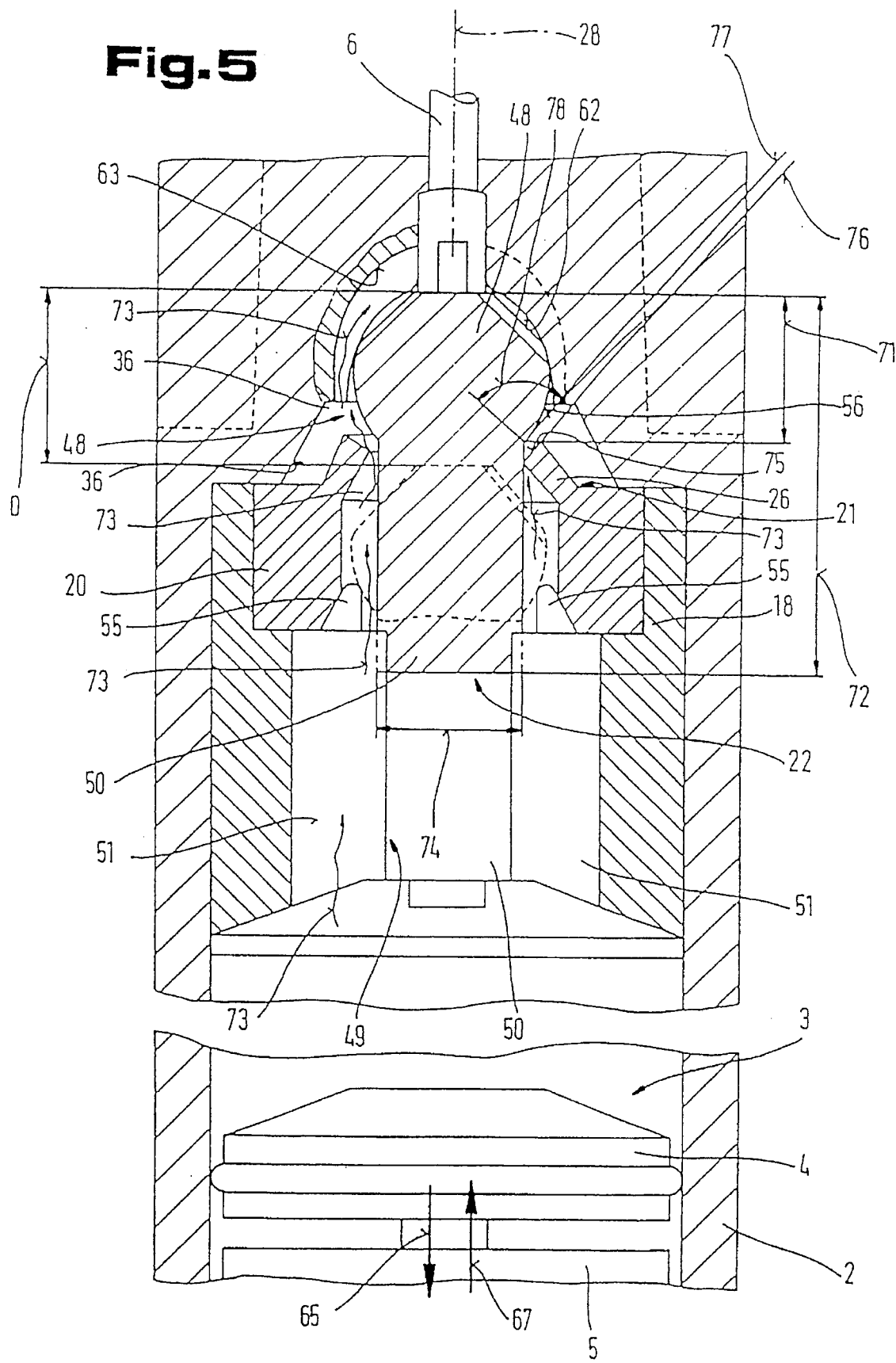

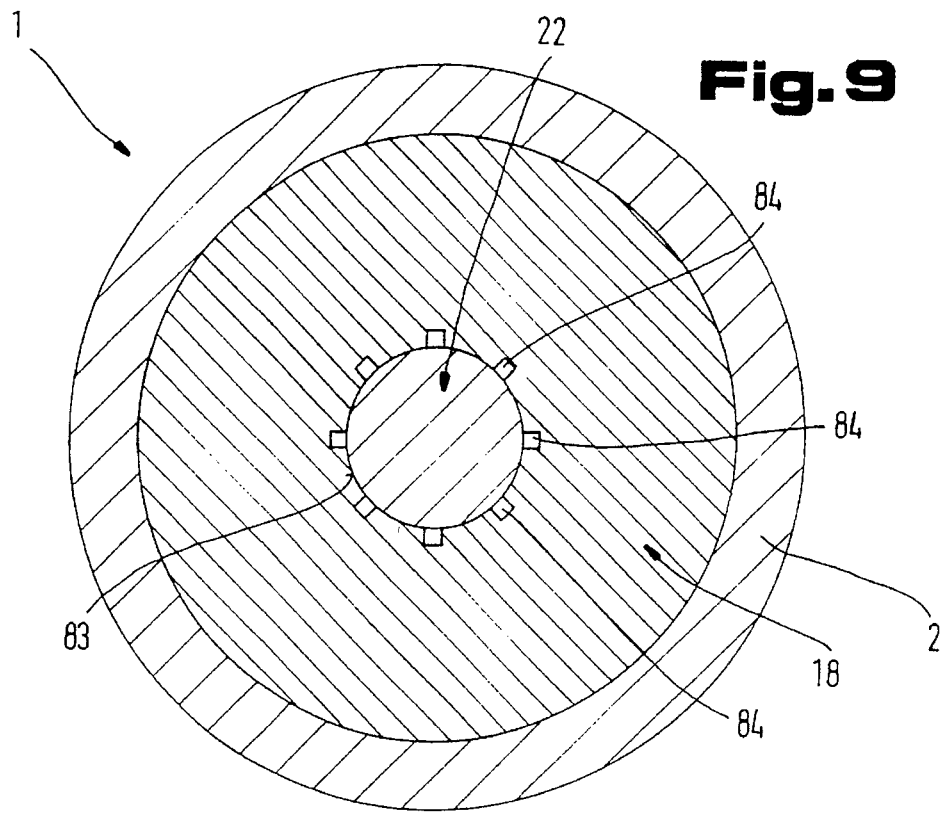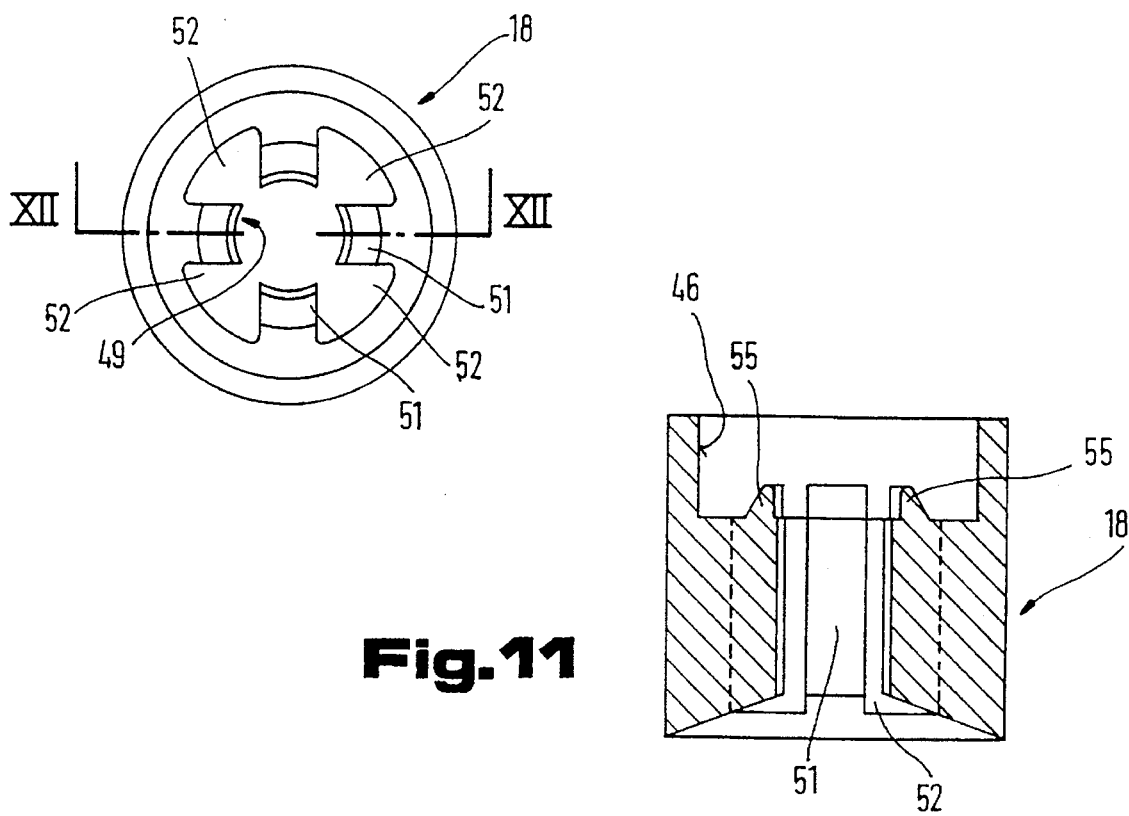

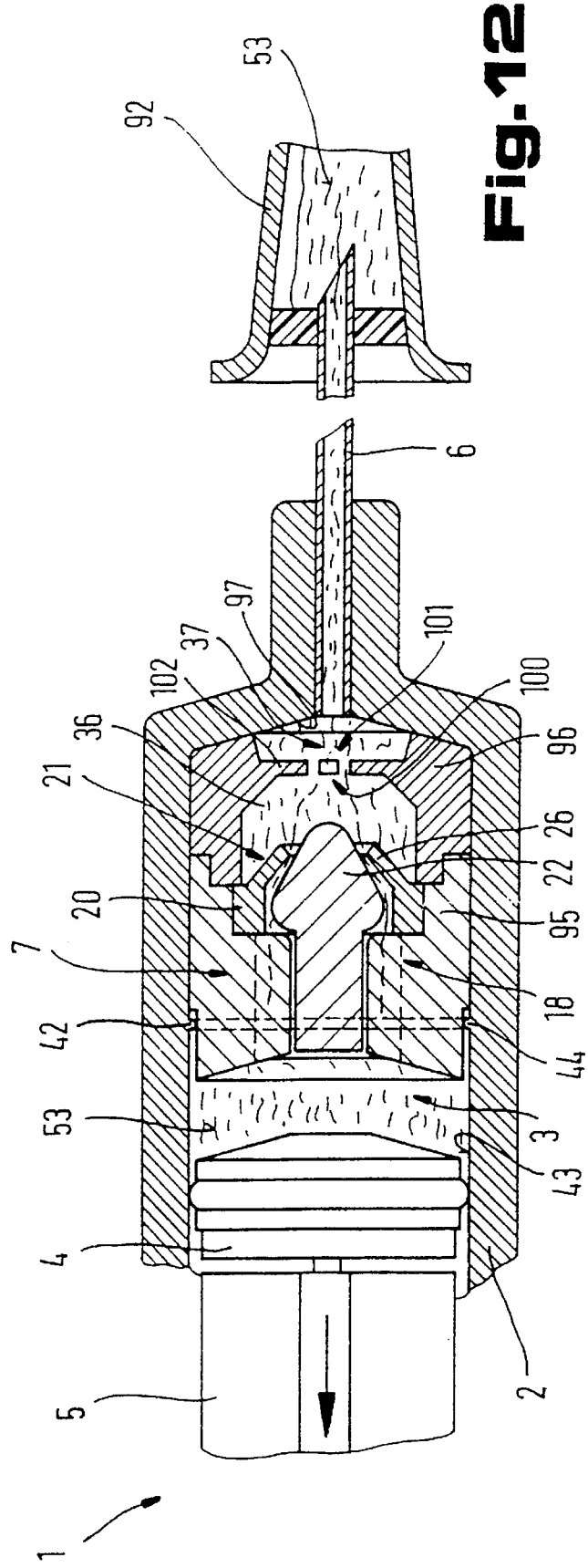

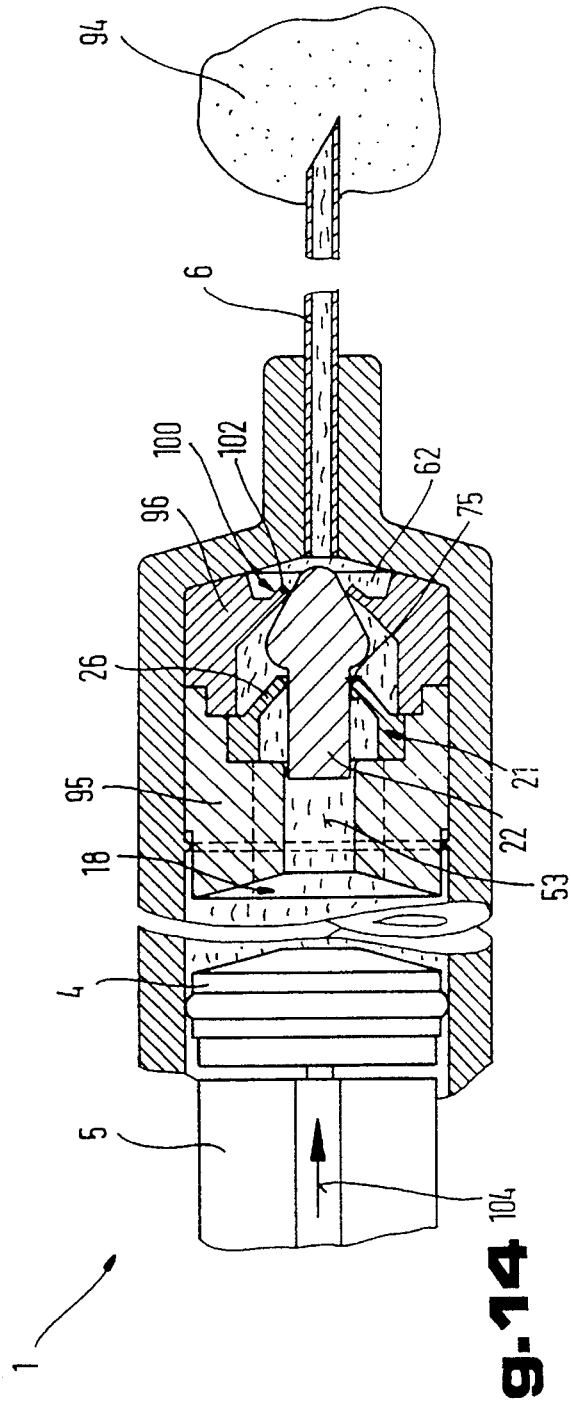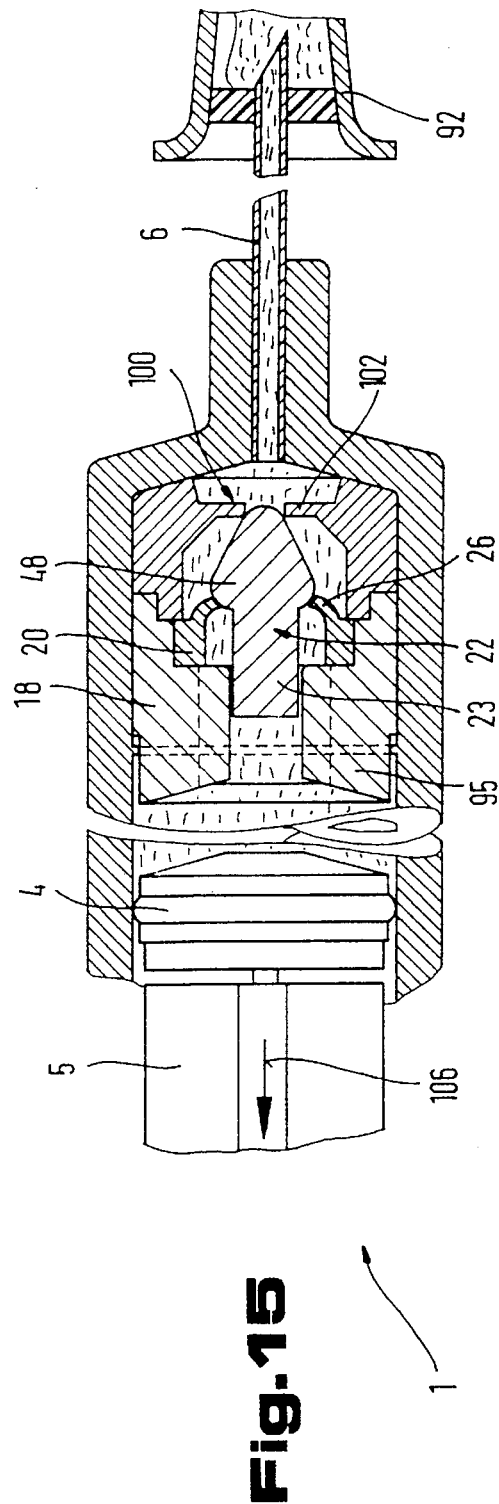

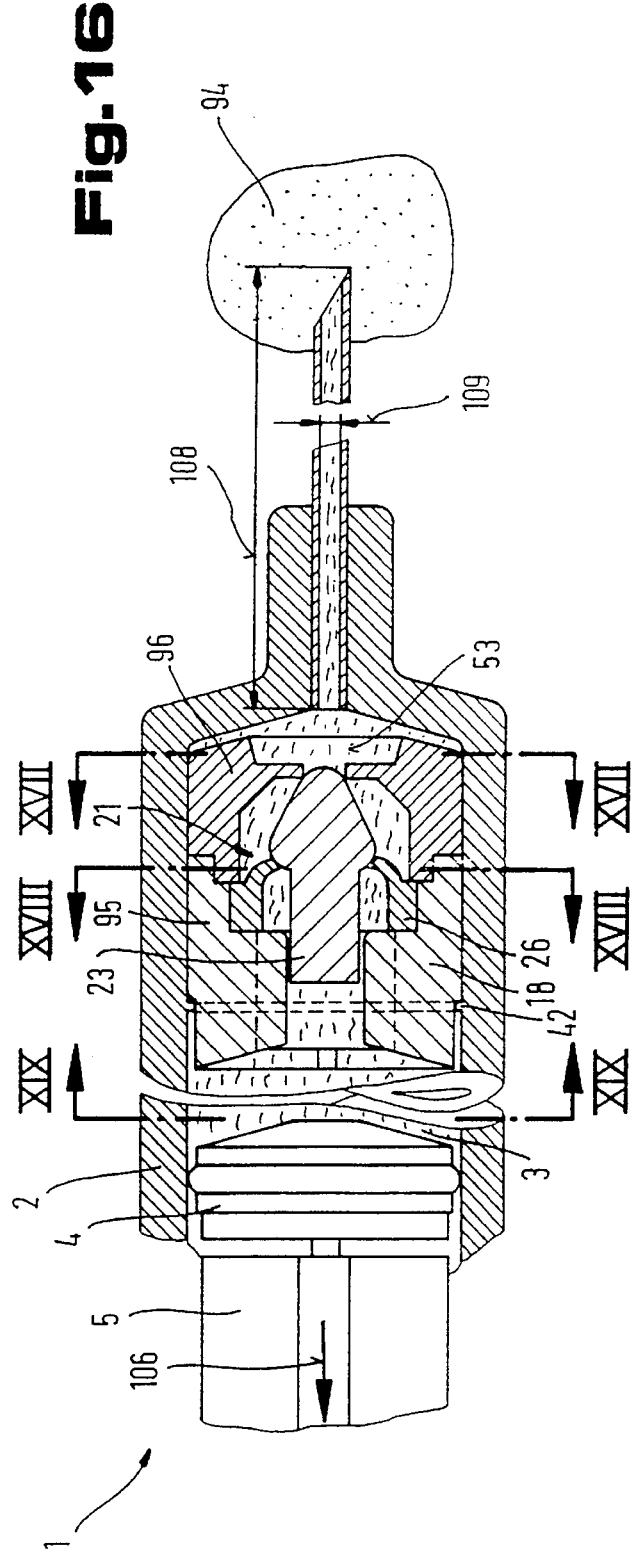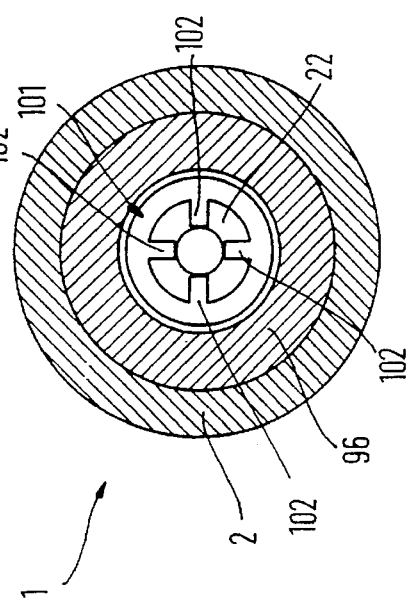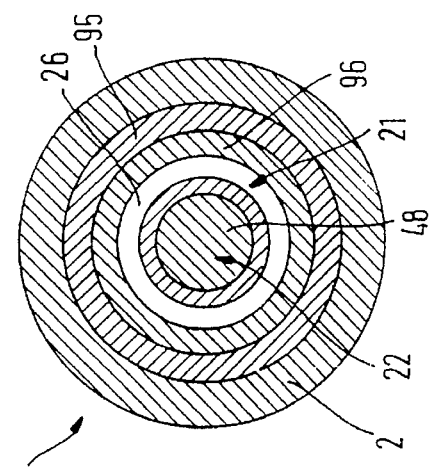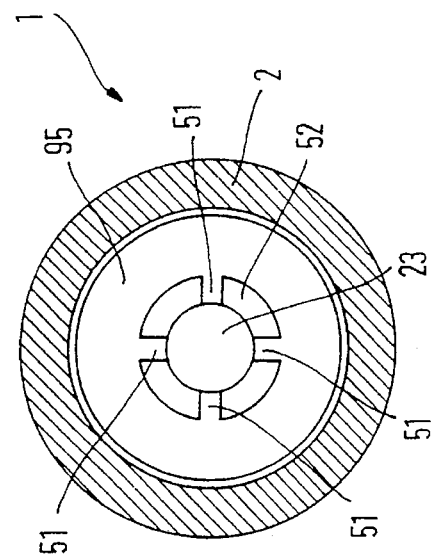

SINGLE USE INJECTION DEVICE

FIELD OF THE INVENTION

The invention pertains to an injection device and more particularly to a single use injection device.

In the case of a known injection device—in accordance with FR-A-26 32 190—an anti-reuse device is used for the prevention of the multiple use of the injection device. This anti-reuse device is placed between the piston-receiving inner space of the injection device and the injection needle, and exhibits a cage and a retaining member for a switching member that is provided in the direction of the piston-receiving inner space of the injection cylinder with a flow-through opening, the diameter of which is smaller than a diameter of the switching member, which is configured as a ball. The retaining member, which is placed on the face of the cage that is turned towards the injection needle, is in the present case an elastically deformable disk with a bore that has an inside diameter that is smaller than the outside diameter of the ball. If now, after the injection medium has been drawn up into the inner space of the injection cylinder, this injection medium is expressed through the injection needle, the full injection pressure acts upon the switching member that is adjacent to the elastically deformable disk, the result of which, because of the large surface of the ball that forms the locking member, this ball, in conjunction with the elastic expansion of the opening of the disk, is pressed through this disk and falls into an intermediate chamber that is connected to it. After the ball has passed through the opening in the elastic disk, the injection medium can now enter past the ball into the hollow needle, or more specifically, the longitudinal bore of the injection needle, and thus be injected. If an additional injection medium were now supposed to be drawn up by the injection device, the piston creates inside the injection needle a negative pressure which, because of the large surface of the ball, acts in such a way that the locking member is now advanced from the injection needle to the elastically deformable disk and lies against it, thus forming a sealing closure. In this way, any further drawing of an injection medium into the inner space of the injection cylinder is prevented. In the area of the cage and in the area of the intermediate chamber that receives the ball after it has passed through the elastic disk, there are, in the direction of the longitudinal axis of the injection device, fixed links or continuations and projecting parts in order to ensure a proper flow- through of the injection medium into the various locations of the locking member when the injection medium is drawn into the inner chamber before the use of the injection device and during the expression of the injection medium through the injection needle during the injection. With an appropriately longer configuration of that part of the intermediate chamber which is located between the cage and the injection needle, an aspiration can be made possible that is dependent on the movement space of the ball in the direction of the longitudinal axis of the injection device. What is disadvantageous about this configuration is the fact that the sure functioning of the injection device is not ensured through the use of an elastic disk, and different mounting parts are needed for each size of injection device.

An additional known injection device of the same type—in accordance with WO-A-92/04064—likewise exhibits an anti-reuse device for the prevention of multiple use of the injection device. The anti-reuse device is again located between the piston-receiving inner space of the injection device and the injection needle, and exhibits a cage that is made of an elastically deformable material, for example, an elastomer, for the retaining member, which is formed by means of a ball. In the cage, a retaining member is formed that is made from a circumferential sealing projection, in conjunction with which a diameter of the bore that is surrounded by the retaining member is smaller than the outside diameter of the ball. This cage, which is made of the elastically deformable material, for example, the elastomer, along with the retaining member that is thus also elastically deformable, is placed through this retaining member into a first and second reception chamber for the ball, which is made of a hard, relatively inflexible material such as glass or stainless steel, into a housing which consists of two housing parts and which is placed into the injection-needle facing end area of the inner space of the injection cylinder. Just as with the previously described FR-OS 26 32 190, any reuse of the injection device following a one-time injection procedure is prevented by virtue of the fact that when the injection medium is expressed from the inner space of the injection cylinder, by means of the hydraulic pressure that is exerted in the ball, this ball is pressed, because of the elastic deformation of the cage and of the retaining member of the elastically deformable cage which is configured as a valve insert piece, through this retaining member from the first chamber into the second chamber. This deformation of the retaining member is encouraged by the design of the retaining member that tapers conically from the first chamber into the second. If an additional injection medium were now to be drawn through the second chamber into the first chamber and thus into the inner chamber of the injection cylinder, the reduced pressure that arises as a result of the drawing back of the piston in the inner space of the injection cylinder, presses the ball from the needle-side second chamber against the retaining member formed by the circumferential projection and is placed on a plane that runs approximately perpendicular to the longitudinal axis of the syringe. The lower pressure that is generated by the drawing up of the piston is then not sufficient to deform the retaining member against the elastic resistance and to allow a passing of the ball from the first chamber through to the second chamber. On the contrary, the opening of the retaining member is closed by the ball, and any further drawing up of an injection medium into the inner chamber of the injection cylinder is thus prevented. In addition, implementation examples are described in which the cage is made of a hard, inelastic material and the switching member is made of a material that is elastic in a radial direction and that can also exhibit a number of sealing sections which are placed one after the other in the longitudinal direction of the switching member. What is disadvantageous about the injection devices in accordance with the two previously mentioned documents is the fact that after the expression of even a small quantity of injection medium from the inner chamber of the injection cylinder, a quantity that may be only slightly larger than the quantity of injection medium needed for aspiration, the anti-reuse device is reliably triggered, and on the other hand, after the triggering of the injection device, a sure seal between the injection needle and the inner space of the injection cylinder—which is supposed to prevent any further drawing up of an injection medium for the multiple use of the injection device—is ensured. In addition, the handling during the injection of injectionmedia into a body should be the same as with the previously known injection devices.

In addition, various injection devices with the widest possible variety of mounting parts and designs are already known that ensure destruction of the injection device after the first use. In that way, multiple uses of the injection devices, and thus infection with epidemic-like diseases, especially AIDS, is to be prevented, especially in countries with little awareness of hygiene. Thus injection devices of that type are known from WO-A 90/03816 and WO-A 90/03817, among others.

SUMMARY OF THE INVENTION

The present invention performs the task of creating an injection device in which a switching organ that can be adjusted between a rest position and a locking position makes possible a sure passing through of the switching member with slight triggering forces and a reliable sealing of the inner chamber against the introduction of an additional injection medium by means of the drawing up of the piston and the lower pressure created by that, or by means of pressure filling.

This task of the invention is carried out by means of the features given in the characterizing portion of Patent Claim 1. The surprising advantage of this solution lies primarily in the retention of the retaining member in a stiff, solid, and elastically non-deformable housing ensuring an exact positioning of the injection device, including the concentric alignment of the opening in the retaining member with the longitudinal axis, so that an evenly tight sealing of the face of the opening against the corresponding contact surfaces of the switching member and its sealing fitting, is ensured. By means of this concentric alignment of the opening of the retaining member, this retaining member is at the same time, however, also aligned concentric to the guiding path track for the guiding fitting of the switching member. At the same time, by means of the design of a guiding fitting that is guided nearly play-free within the guiding path of the housing, it is ensured that the switching organ itself, or more specifically, its sealing section, is also aligned concentrically with the opening and ensures a constant contact pressure between the switching member and the retaining member at the entire perimeter. Thus there is a perfect seal between these two parts both before the passing of the switching member through the retaining member as well as after the passing of the sealing section of the switching member through the retaining member. This surprising discovery of the present invention make it possible that, primarily as a result of the exact sealing between the retaining member and the switching member, or more specifically, its sealing section, against the passing of the same through the retaining member, a forward feeding force that always remains constant can be transmitted from the piston of the injection device through the medium to the switching member. As a result it is ensured that at the first actuation, that is, at the beginning of the expulsion of the medium from the inner chamber of the injection cylinder, the switching organ, or more specifically, its sealing section, reliably passes the retaining member, and thus brings about the destruction of the anti-reuse device, and the injection device is made unusable for any additional use. Another surprising advantage of this apparently simple solution in accordance with the invention lies in the fact that, as a result of the layout of the anti-reuse device, both the guiding fitting as well as the guiding path in the housing can be made from a hard material with correspondingly favorable sliding characteristics. As a result, the frictional resistance, that is, the force that works against the proper passing of the switching organ, especially its sealing section through the retaining member, can be kept as small as possible. As a result, the proper triggering or operation of the anti-reuse device can be ensured with the expression forces for the medium that are common for normal injection devices. In conjunction with this, it is at the same time possible to dispense with the use and the usage of additional sliding means between the switching member and the housing or the retaining member, as a result of which the use of this injection device is also possible even with media that cannot be used in conjunction with such sliding means. As an advantageous result of the concentric alignment of the opening of the retaining member with the longitudinal axis of the guiding path after the passing through of the sealing section of the switching member, the retaining member, especially its supporting ring can be guided at the guiding fitting in a centered manner. As a result of this contact against the guiding fitting, a free discharge of the medium from the inner chamber of the injection cylinder is prevented and, immediately upon any movement of the piston exerted counter to the direction of ejection of the medium, a flow of the medium back into the inside of the injection cylinder is stopped at once. This constant support and central alignment of the supporting ring of the retaining member also means that, even after a lengthy period of non-use of an already used injection device, the supporting ring is positioned so exactly that if an attempt is made to draw up a medium for the reuse of the injection device, the sealing section will even then bring about a permanently sealed closure as a result of the tight contact against the retaining member, achieving the high operational reliability of this anti-reuse device. In this way it is also possible to prevent the injection device from being refilled by means of pressure filling, for example. This is encouraged by the fact that the outflow pressure is higher than the suction vacuum. In addition, when the injection device in accordance with the invention is used, even the dead volume, which is understood to mean the volume which remains between the side of the piston that is facing the injection device and the outlet opening of the injection needle following the complete expression of the medium from the inner chamber of the injection cylinder—that is, when the piston lies against the front face of the anti-reuse device—and can no longer be expressed. The layout of the anti-reuse device is designed in such a way that even when the same device is used, the maximum values prescribed in the standards for this dead volume are not exceeded.

A configuration in accordance with Patent Claim 2, in which a tilt-resistant guiding of the switching member is attained, is also advantageous. As a result, a single-sided loading of the retaining member is reduced, and a sure, stick-free triggering of the switching member is attained.

An additional possible design is described in Patent Claim 3, as a result of which manufacture of the switching member with somewhat larger tolerances for guiding in the housing is possible. The further development in Patent Claim 4 is distinguished by the fact that jamming between the switching member and the retaining member, primarily before the sealing section passes through the retaining member, can be prevented.

Also advantageous is a further development in accordance with Patent Claim 5, since, with it, the proper evacuation of air from the injection device in accordance with the invention is achieved on the one hand, together with preventing a false triggering of the switching member to take place before an appropriate pressure for expulsion of the medium is created by means of the injection device, and on the other hand, the anti-reuse device cannot be activated.

The design in accordance with Patent Claim 6 makes it possible, along with contact of the switching member on the side facing the inner chamber, for a flow of the medium under pressure by means of the piston to occur in a radial direction. As a result the surface available for the pressure contact increases, and thus a sure triggering of the anti-reuse device is achieved.

Because of the implementation variant in accordance with Patent Claim 7, it is possible to manufacture the anti-reuse device with a small number of individual parts, such that it can be built into the injection cylinder.

An advantageous further development is achieved by means of the design in accordance with Patent Claim 8, as a result of which automated assembly is made possible.

A design in accordance with Patent Claim 9 is also possible which achieves a subassembly that makes automated assembly easier.

Another advantageous development is described in Patent Claim 10, through which the housing parts can be inexpensively joined. An advantageous further development, as described in Patent Claim 11, makes possible the design of very effective sealing surfaces with a short length for the sealing section.

Also possible is a design in accordance with Patent Claim 12, through which a corresponding widening effect is attained for the penetration of the sealing member through the supporting ring, even at low liquid flows.

Preferable implementations in accordance with Patent Claims 13 and 14 are also possible which achieve a flow-enhancing gradation of cross-sections in the direction of flow.

An advantageous further development is described in Patent Claim 15, by means of which the switching member in its installed state is centrally guided at a distance that is greater than that corresponding to the length of the guiding path, and after the switching, a more reliable seat is attained for the sealing to prevent refilling.

Also possible with that is a design in accordance with Patent Claim 16, because the switching process is simplified by means of it.

In accordance with the design in accordance with Patent Claim 17, an unhindered elastic deformation of the supporting ring during the switching process is attained.

In accordance with an advantageous further development corresponding with Patent Claim 18 or 19, a fault-free manner of operation is achieved, even when dimensional deviations occur in the elements as a result of the manufacturing process.

Corresponding to the design in accordance with Patent Claim 20, an unintentional resetting of the switching member into its initial position is effectively prevented, in conjunction with which the resistance against a resetting increases in an approximately linear manner with the force load that is used for a procedure of that type.

An advantageous further development is described in Patent Claim 21, as a result of which additional components and thus costs are cut. By means of the design in accordance with Patent Claim 22, a positionally secure retention of the switching member in the locking position is attained.

Possible in conjunction with that is a design in accordance with Patent Claim 23, by means of which the proper manner of operation of the components that prevent refilling does not require any additional operating force, or more specifically, there is no increase in these forces.

Also advantageous, however, is a design in accordance with Patent Claim 24, by means of which a good adaptation of the dynamic effect for the resetting for injection devices of different standard sizes is achieved.

Also offering an advantage, however, is a design in accordance with Patent Claim 25, by means of which a positioning is achieved in the inner chamber in the region of the front wall that faces the injection needle and in the longitudinal direction of the injection device.

By means of the design as it is described in Patent Claim 26, the aspiration procedure is possible by means of the ability of the housing to slide longitudinally with the switching member without expensive design and construction measures being necessary.

In accordance with the design in accordance with Patent Claim 27, the volume that is necessary for a proper aspiration procedure can be matched to the necessary conditions.

The advantageous further development corresponding to Patent Claim 28 makes possible an axial play of the switching member in its locking position, which makes the aspiration procedure possible, but, in addition to that, also effectively prevents any refilling of the injection device.

In accordance with an advantageous further development corresponding to Patent Claim 29, the complete expression of air that may also have been drawn in is achieved before the administration of the injection medium. Corresponding to a further development as it is described in Patent Claim 30, a proper concentricity of the guiding path with the inner chamber of the injection cylinder is achieved early in the manufacturing process, and is not affected by the manufacturing tolerances of additional components such as the housing for the switching member, for example.

In accordance with the advantageous design corresponding to Patent Claim 31, the manner of operation of the injection device in accordance with the invention is reliably achieved.

Also advantageous, however, is a design as it is described in Patent Claim 32, because a design of that type is advantageous for the design of the tools that are needed for the manufacturing.

Also possible, however, is a design in accordance with Patent Claim 33, because as a result, flat projection angles are attained during the administration of the injection medium, even with injection devices having a large volume.

Corresponding to an advantageous further development in accordance with Patent Claim 34, a matching of the flow-through capabilities between a medium of low viscosity, such as air, and a medium of higher viscosity, that is, the medium to be administered, is achieved.

In accordance with a further development corresponding to Patent Claim 35, an inexpensive manufacturing possibility for the pass-through channel is achieved.

Finally, however, a design in accordance with Patent Claim 36 is also advantageous, because by means of it, the pass-through cross-section for the pass-through channel is distributed over a larger length of perimeter of the retaining member, as a result of which uneven flow conditions are prevented.

BRIEF DESCRIPTION OF THE DRAWINGS

The invention is described in more detail in the following with the aid of the implementation examples represented in the drawings.

The following are shown:

FIG. 2 a part of the injection device in accordance with FIG. 1 in a side view, cross section and in enlarged scale, in a position of the switching member for drawing up a medium into the inner chamber of the injection cylinder;

FIG. 5 the injection device in accordance with FIGS. 2 through 4 during the expression of the medium through the injection needle;

FIG. 9 the injection device in accordance with FIG. 8 in the region of the channels that run parallel to the guiding path, shown in front view, a cross section in accordance with the lines IX—IX in FIG. 8;

FIG. 10 the housing with the guiding path for the switching member with retaining member left out, shown in top view;

FIG. 11 the housing in side view, cross section in accordance with the lines XI—XI in FIG. 10;

FIG. 12 a part of a different form of implementation of the injection device in side view, cut away and in enlarged scale, in a position of the switching member for drawing a medium into the inner chamber of the injection cylinder;

FIG. 14 the injection device in accordance with FIG. 12 or 13 in the region of the switching member with the position of the switching member and the retaining member during expression of the medium;

FIG. 15 the injection device in accordance with FIGS. 12 through 14 during an attempt again to draw a medium up into the inner chamber of the injection cylinder after the expression of the medium originally drawn up;

FIG. 16 the injection device in accordance with FIGS. 12 through 15, during the drawing back of the piston for aspiration;

FIG. 17 injection device in front view, cut away in accordance with the lines XVII—XVII in FIG. 16;

FIG. 18 injection device in front view, cut away in accordance with the lines XVIII—XVIII in FIG. 16;

FIG. 19 injection device in front view, cut away in accordance with the lines XIX—XIX in FIG. 16;

DETAILED DESCRIPTION OF THE PREFERRED EMBODIMENTS

Figure 1:
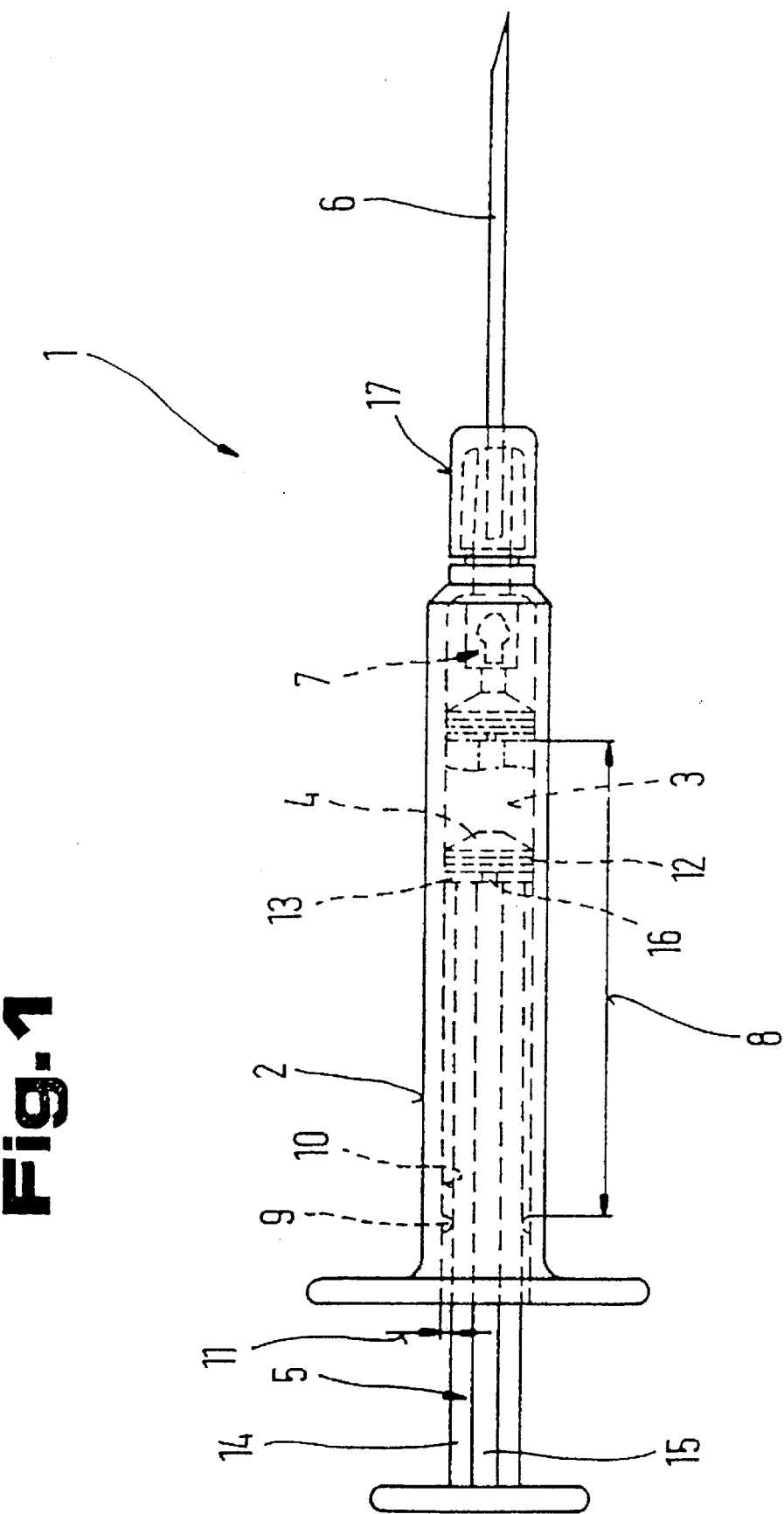
FIG. 1 an injection device designed in accordance with the invention in side view and in simplified, schematic representation.

In FIG. 1, an injection device 1 is shown, which exhibits an injection cylinder 2 and a piston 4 that can travel inside the inner chamber 3 of the cylinder, which piston can be actuated by means of a piston rod 5. In an outlet region of the injection cylinder 2 facing an injection needle 6 there is provided an anti-reuse device 7, which is drawn in schematically. Multiple use of the injection device 1 is to be prevented by means of this anti-reuse device 7.

By that is meant that, following the drawing up of a first injection medium into an injection device 1 that has for example been supplied empty, and its expression in the course of an injection procedure, any further injection medium can no longer be drawn up into nor pressed up into the inner chamber 3 of the injection device 1.

By means of this prevention of multiple uses, it is primarily infection with contagious diseases and primarily AIDS, that is to be prevented during inoculations or the administration of long-term medications such as insulin, for example. This anti-reuse device 7, which is described in the following with the aid of an injection device 1, and with which, in a preferred manner, the injection cylinder 2 is made of plastic, can of course also be used with injection devices 1 with, preferably, siliconized injection cylinders 2 made of glass.

In conjunction with this, however, it is also possible to provide the injection cylinder 2 with a coupling apparatus for any kind of detachable injection needles, for example, a Luer cone, in order to attach the injection needles 6, which can be placed in a protective sheath, only just before using of the injection device 1. On the other hand, it is of course also possible for the injection needles 6 to be joined directly with the injection cylinder 2, for example, bonded, injection molded, or poured.

A stroke 8 of the piston 4 is limited in the direction away from the injection needle 6 by means of limit stops 9, which project beyond an inner surface 10 of the injection cylinder 2. A height 11 of these limit stops 9 is dimensioned in such a way that they retain the piston 4 in the region of a circumferential piston ring 12, in particular, an O-ring. It is, however, just as possible for the limit stop 9 to act in conjunction with a,piston body 13, and for that purpose, to mesh between the fixed links 14, 15 of the piston rod 5; these fixed links are usually placed at 90° to each other.

With an appropriate design of the height 11 of the limit stops 9, it can be ensured that during an attempt to draw the piston 4 from the inner chamber 13 of the injection cylinder 2, the tractive force that is exerted via the piston rod 5 is so high that a weakening location 16 between the piston rod 5 and the piston 4 can no longer transmit this tractive force to the piston 4, and breaks. In this way it is ensured that any improper use of the injection device 1, even by means of the withdrawal of the piston 4 and the filling of the inner chamber 3 from the piston rod side, is prevented.

In FIG. 2, only a part of the injection device 1 is shown, in enlarged scale. Thus, in FIG. 2 only the end region of an inner chamber 3 of the injection cylinder 2 facing the injection needle 6 is shown.

The anti-reuse device 7 includes a housing 18, between which and a projection 19 in the injection cylinder 2 is placed, preferably designed as a disk 20, a retaining member 21 for the switching member 22 with a guiding element 23. The anti-reuse device 7 can also be formed as a one-piece component, whereby the housing 18 then forms a one-piece component with the retaining member 21. By means of the division of the anti-reuse device 7 into the housing and the retaining member 21, the most appropriate materials can be used for the particular case in question.

In the usual manner, the housing 18 is made of a harder plastic 24, which exhibits, for example, a modulus of elasticity of over 2000N/mm$^2$ and a Shore A hardness of more than 90 and a Shore D hardness of more than 70. In the same way, the switching member 22 is likewise made of the same kind of hard plastic, and specifically, a thermoplastic or duroplastic material, whereby the duroplastic material can be recommended both for the housing 18 as well as for the switching member 22, since they are not temperature dependent, and if they have been hardened in an organic solvent, they do not decompose.

In contrast with that, the retaining member 21 and the disk 20, which in this form of implementation are preferably designed as a one-piece component made from a softer plastic 25, namely, a so-called elastomer. This is a molding material that remains soft and rubbery over a sufficient range of service and ambient temperatures. Slight tensile forces bring about considerable deformations, but after the tensile force is removed they return almost completely to the original dimensions. They do not flow even when the temperature increases, but instead remain elastomeric to the border temperature of irreversible chemical decomposition. Chemically cross-linked elastomer products or thermoplastic elastomers can be used for this. The Shore A hardness is between 20 and 60.

Of course, it is also possible that it is not the entire disk 20 that is made of this plastic 25, or more specifically, the elastomer, but rather only a supporting ring 26, which projects past a through-bore 27 in the disk in the direction of the longitudinal axis 28 of the injection device 1. In this case it is advantageous if the supporting ring 26 is formed on the disk 20, or if the disk is being dispensed with, on the housing 18 or on a part of the housing.

The support is configured as a hollow cone section, and exhibits an inner surface 29, an opening angle 30, which is greater than an opening angle 31 of an outer surface 32. An opening 33 exhibits a diameter 34 that is smaller than a diameter 35 of the through-bore 27. The supporting ring 26 projects into an open space 36 that is located in an inlet area 37 of the injection device 1 and that extends from the projections 19 in the direction of the injection needle 6. In addition, this open space 36 is dimensioned in such a way, that is, it exhibits a width 38, such that it ensures that the supporting ring 26 does not come to rest against a limiting wall 39 even if its inner surfaces 29 run parallel to the longitudinal axis 28, as is shown in FIG. 2 by means of dashed lines.

The supporting ring 26, which is designed as a hollow cone section, preferably exhibits in the region of its opening 33 a greater wall thickness than at the base of the hollow cone section. In conjunction with this, it has proven to be advantageous if the wall thickness at the base amounts to about 0.2 mm and conically expands to about 0.3 mm in the region of the opening 33. In this way, on the one hand a favorable deformation behavior is attained with, preferably, low actuating forces in the transitional region to the disk 20 or the housing 18, and on the other hand, sufficient width of the sealing surface in the front end region is achieved for the arrangement, and for a perfectly tight sealed closure between the retaining member 21 and the switching member 22. The more solid sealing surface resulting from the greater width also prevents any pressure filling through the injection needle 6.

In contrast, an outside diameter 40 of the disk 20 is greater than an inside diameter 41 of the open space 36, so that the disk 20 and the housing 18 are supported by the projections 19 in the injection cylinder 2. The anti-reuse device 7 is undisplaceably positioned in the inlet area 37 of the injection cylinder 2 by virtue of the fact that the disk 20 and the housing 18 are supported on the one hand against the projections 19 at the front wall of the injection cylinder 2, and in the opposite direction, that is, towards the piston 4, the housing makes contact by means of a limit-stop part 42, for example, a collar 44 that protrudes over an inner surface 43 Of the injection cylinder 2. The housing 18 is thus clamped between the projections 19 and the limit stop 42. The setting of the housing 18 into the inlet area 37 of the injection cylinder 2 is carried out by pressing in the housing 18, whereby either the housing 18 or the injection cylinder 2 is correspondingly deformed until the housing 18 is locked into place behind the limit stop part 42.

The disk 20 is in turn set into a recess 46 in a face 47 of the housing 18, so that the face of the disk 20 facing the projections 19 preferably runs flush with or even with the face 47.

Figure 3:
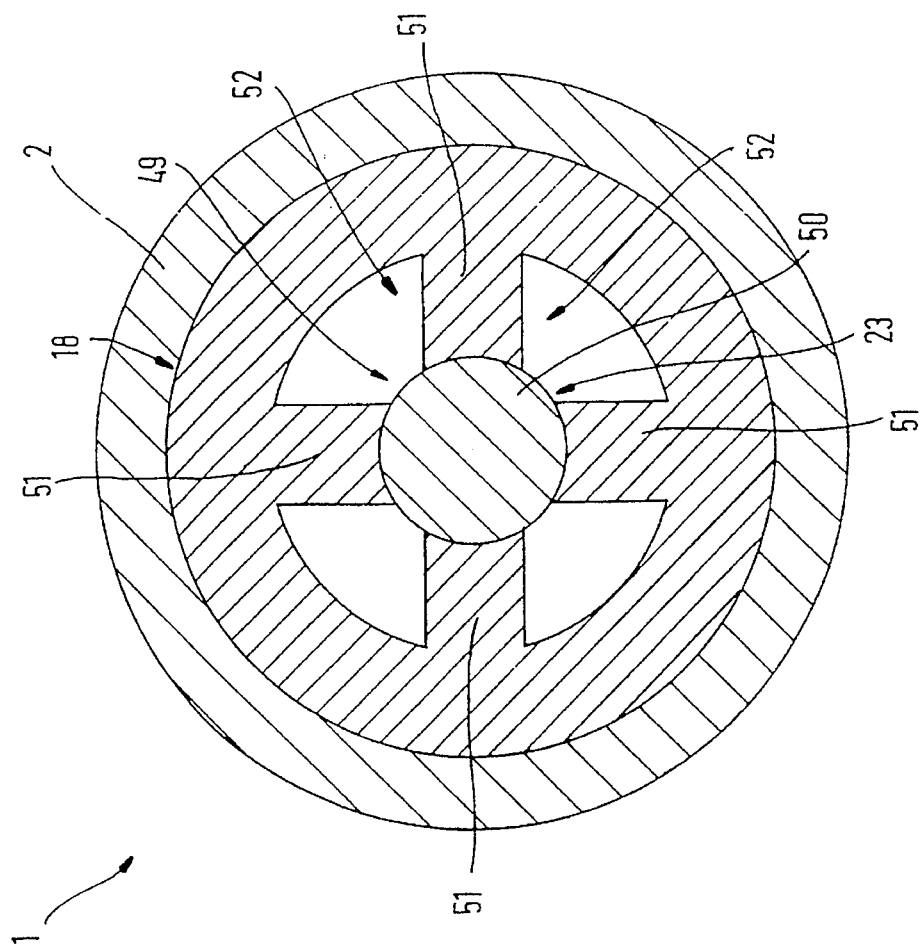
FIG. 3 the injection device in the region of the guiding path in front view, a cross section in accordance with the lines III—III in FIG. 2.

The switching member 22 in turn consists of a sealing section 48 and the guiding element 23. This guiding element 23 is guided in a guiding path 49 in the housing 18. As can be better seen in FIG. 3, this guiding path 49 for the guiding element 23 that is formed by the guiding pin 50 is formed by fixed guiding links 51, which are displaced by 90° to each other, of the housing 18. Between the individual fixed guiding links 51 there are formed channels 52 through which a medium 53 can pass from the inner chamber 3 of the injection device 1 to the injection needle 6. The guiding path 49 is thus produced by means of a partially interrupted guiding bore which is formed by the fixed guiding links 51 and in which the guiding pin 50 can be moved without leeway in the direction of the longitudinal axis 28. This guiding path 49 is preferably produced with a very exact fit, or more specifically, with tolerances that are in the range of less than 0.1 mm, preferably in the range of less than 0.01 mm, so that over a complete guiding length 54, over which a guiding length 54 of the guiding element 23 and a guiding length 54 of the guiding path 49 overlap each other, a centered guiding of the switching member 22 is ensured. This accuracy in the guiding between the switching member 22 and the guiding path 49, as will be explained in more detail in the following, also brings about a trouble-free cooperation between the supporting ring 26 and the sealing section 48 of the switching member 22.

This centered guiding of the switching member 22 is supported by guiding lugs 55, which project from the fixed guiding links 51 in the direction of the disk 20 and which support and hold centered the sealing section 48 in the region of its surface 56, which is, for example, formed by a calotte shell section. The disk 20 can be provided with corresponding cutouts in order to receive the guiding lugs, but it is also equally possible to produce the disk without cutouts, as a result of which the guiding lugs 55 are used at the same time for the centering of the disk 20 during the insertion of the housing 18 between the projections 19 and the limit stop part 42. With this, there is also achieved a displacement of the disk 20, which is made from an elastomer and is elastically deformable, and which thus represents a flaccid bending part even during a lengthy period of storage, or more specifically, an improved clamping of the disk, especially during the pressing of the sealing section 48 through the opening 33 of the supporting ring 26.

The sealing segment 48 that is now designed as a calotte shell section in the region of the surface 56 on the side facing the guiding element 23 is provided in its end region facing the supporting ring 26 with a surface 57 that is designed as a truncated cone.

In conjunction with that, a diameter 58 is smaller than an inside diameter 34 of the opening 33, whereas an outside diameter 59 of the sealing section 48 is greater than the diameter 34 of the opening 33. The outside diameter 59 corresponds to the diameter of the calotte shell section of the surface 56 many times over.

Figure 4:
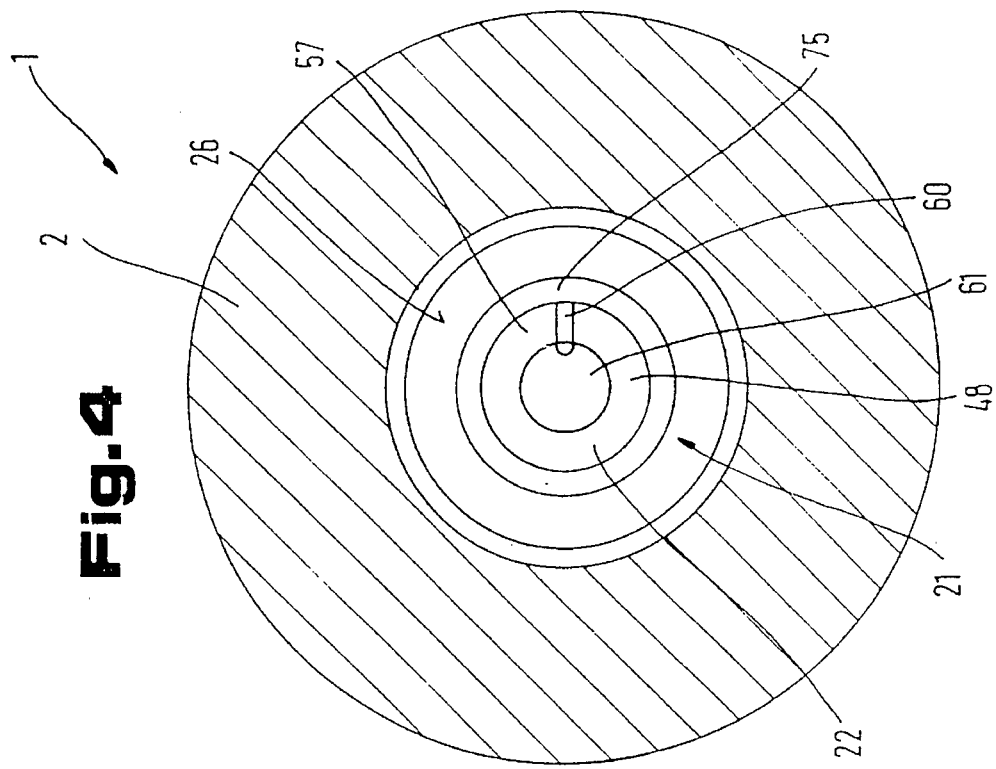
FIG. 4 the injection device in the region of the retaining member, in front view, cut away, in accordance with the lines IV—IV in FIG. 2.

The manner of functioning of the injection device 1 in accordance with the invention is described in the following in more detail with the aid of the representations in FIGS. 1 through 6:

In the surface 57 of the truncated cone 56 running in the direction of a side edge, or more specifically, parallel to a side edge or surface of the same—which can best be seen in FIG. 4—there is placed a de-airing channel 60, which extends from the surface 56 that is designed as a calotte shell section to the region of a face surface 61 of the sealing section 48.

At the open space 36 in the direction of the injection needle 6 there is also attached a reception chamber 62 for at least the sealing section 48 of the switching member 22. As can be seen in the drawn representation, particularly in FIG. 2, a spatial formation of this reception chamber 62 is chosen in such a way that it corresponds, at least in its inner dimensions, with the outer dimensions of the sealing section 48. In addition, there are placed adjacent to this reception chamber 62 guiding channels 63, past which the injection medium can flow outward in the direction of the injection needle 6, even if the sealing section 48 is located in this reception chamber 62.

In addition, there is shown in the represented implementation example a piston 4, that is equipped with an O-ring 64 that is designed as a piston ring 12 and made, for example, of plastic and inserted into the piston 4. It is in this implementation that the design of the weakening section 16 between the piston rod 5 and the piston 4 can be seen as well.

If now, as can better be seen from FIG. 2, for example, a medium 53 is drawn from an ampoule that is not shown—such as is shown in FIG. 12 for a different form of implementation—into the inner chamber 3 of the injection cylinder 2, then in addition, the piston rod 5 along with the piston 4 that is attached to it has to be moved away from the injection needle in the direction of the arrow 65. As a result, there is built up in the inner chamber 3 of the injection cylinder 2 a lower pressure, which brings about a drawing back of the switching member—even if the switching member 22 were to have been lying against the supporting ring 26 during the transporting of the injection device 1—into the position shown in FIG. 2 in solid lines. At the same time, as a result of the lower pressure brought about by the drawing back of the piston 4, as is indicated schematically by the arrow 66, the medium 53 is drawn all the way through the injection needle 6, through the reception chamber 62 between the supporting ring 26 and the sealing section 48 of the switching member 22, and in addition, through the channels 52—FIG. 3—and into the inner chamber 3 of the injection cylinder 2.

As soon as the ampoule has been emptied, or more specifically, as soon as a sufficient quantity of the medium 53 is present in the inner chamber 3, this medium can now be expressed from the inner chamber 3 by virtue of the fact that the piston 4 is moved with the piston rod 5 in the direction of the arrow 67. By means of the hydraulic pressure that is building up as a result of this, via a face 68 of the switching member that is facing the inner chamber 3 of the injection cylinder 2, a forward feeding force is exerted on the switching member 22, and corresponds to the pressing force being exerted, the value usually provided being 5N–10N, or more specifically, 7.5N, it is thus ensured that in every instance, as a result of a high pressing force of that type, that the switching member 22 will be pushed forward in the direction of the injection needle 6, until its surface 57 lies in a sealing manner against the inner surface 29 of the supporting ring 26 of the retaining member 21.

Of course, in practice, even a substantially lower value for the force to be exerted, that is, it lies significantly below the maximum value of 7.5N–10N, is usually sufficient to produce a tight seal between the inner chamber 3 and the injection needle 6 immediately after the actuation of the piston 4 in the direction of the arrow 67, so that no medium 53 can come out through the injection needle 6. These small forward feeding forces are usually sufficient, since the switching member 22 is also streaming against not only on the face 68, but also, in accordance with the arrow 69, via the channels 52 of the sealing section 48, that is, the part that projects over the perimeter of the guiding element 23 in the region of its surface 57—as is shown schematically by the arrow 69—both tangentially and sideways, and thus the total force being exerted by the medium 53 for the creation of a forward feeding movement of the switching member 22 is sufficient in every instance to ensure a movement of the switching member in the direction of the supporting ring 26.

Before a medium 53 can now be administered with the injection device 1 in accordance with the invention, the injection device 1 has to be de-aired. To do this, the injection device is usually brought into a slanted position in which the injection needle 6 is located at the highest point. In addition, the occlusions of air that are present in the injection medium can be made to collect in the upper end area and to come out of the injection device by means of a light tapping on the injection cylinder 2. At the same time, a light force is exerted on the medium 53 via the piston rod 5 and the piston 4 by the user of the injection device 1. However, because of the configuration of the injection device 1 in accordance with the invention, there is brought about between the switching member 22 and the supporting ring 26 an exactly sealing closure, which can also be primarily attributed to the fact that the opening angle 30 of the inner surface 29 of the supporting ring 26 is greater than an opening angle 70 of the truncated cone of the switching member 22. As a result of the smaller diameter 58 of the face surface 61, when the switching member 22 enters into the opening 33, the latter widens somewhat until the inner surface 29 with the smaller opening angle 30 fits snugly against the surface 57 of the sealing section 48, which is designed as a truncated cone.

In order to now make possible, in spite of this, a proper de-airing of the medium 53 in the inner chamber 3 of the injection cylinder 2, at least one de-airing channel 60 is provided along one of the side edges of the truncated cone.

As indicated in FIG. 2 by means of dashed lines, the de-airing channel or channels extend from outside the sealed region into the open space 36, so that air bubbles that are under a slight pre-stress pressure from the piston 4 can come out of the inner chamber 3 in the direction of the injection needle 6, through the injection needle 6 as a result of the vibrations that are caused by the taps on the injection cylinder 2, and into the open.

In the design of the de-airing channel or channels, specifically, there can also be several de-airing channels 60 provided, consideration has to be given to the viscosity of the injection medium at hand. Making use of professional knowledge, it is specifically the cross-section of the particular de-airing channels 60 under consideration that must be established, taking into consideration the viscosity of the injection medium to be injected by means of the injection device 1, in such a way that the friction losses based on the adhesive force of the liquid at the surface must be designed in such a way that, with the exertion of a pressing force by the user on the piston rod 5 and the piston 4, which lies under that force which is necessary to move the switching member 22 through the retaining member 21, no injection medium can pass through the de-airing channel 60. The de-airing channels, or more specifically, their cross-sectional form, must thus be designed in such a way that they are liquid-tight with respect to the liquid injection medium to be used.

At the same time, care must be taken, with highly viscous injection mediums, for example, that the cross-section of the de-airing channels is not selected by making full use of the available cross-sectional areas in order to prevent a strong reduction of pressure, which would lead to the fact that the pressing force that can be brought to bear by the piston 4 would not be sufficient to displace the switching member 22 from the rest position shown in FIG. 2 into the locking position shown in FIG. 5.

If the user's force on the piston is then so strongly increased that an injection medium can be administered, into the body of a patient for example, that is, can be expressed through the injection needle 6 even independently of that, then the forward feeding force exerted by the arrow 69 is strongly increased until the forward feeding force is sufficient to elastically expand the supporting ring 26, which acts as a sealing membrane, far enough in the radial direction and in the direction of the injection needle 6 that the sealing section 48 can pass through the opening 33 in the supporting ring 26. By means of the simultaneous guiding of the switching member 22 with the guiding pin 50 in the guiding path 49, an even expansion of the opening 33 over the entire cross-sectional area is attained, and prevents, above all, that as a result of a tipping of the sealing section 48 in the region of its end which is designed in the form of a truncated cone, the injection medium can come out through the opening 33, but the switching member 22 does not penetrate the opening 33.

To achieve that, the guiding length 54 is designed in such a way that it is greater than a distance D between the rest position shown in dashed lines in FIG. 5 and the frontmost locking position, shown in the same figure, in the direction of the injection needle 6. In conjunction with that, the position shown in dashed lines in FIG. 5 corresponds to the position shown in solid lines in FIG. 2. However, the guiding length 54 must at least correspond to a length 71 of the sealing section 48.

Along with that, care must also still be taken that the guiding length 54 is designed in such a way that over the entire displacement path, that is, the distance D, a tip-proof, axis-parallel guiding of the switching member 22 is ensured along, that is, parallel to the longitudinal axis 28 and the longitudinal axis of the guiding path 49.

Naturally, it is also possible that the axis, that is, the longitudinal axis of the guiding path 49, does indeed run parallel to, but displaced sideways from, the longitudinal axis 28 of the injection needle 6 or the injection device 1. In this way, it is possible to prevent that, through the introduction of a mechanical pushing member or something similar from the side of the injection needle 6, the switching member 22 can be pushed by force from its locking position back into its rest position in accordance with the representation in FIG. 2. However, it is of course also possible that by means of the installation of baffle plates that are displaced with respect to each other and that overlap each other, or by means of displaced slots, a mechanical resetting of the switching member 22 can be prevented.

In addition, care must also be taken that a total length 72 of the switching member is at least greater than the outside diameter 59, or more specifically, the maximum outside diameter of the switching member 22. It is only in that way that it can be ensured that the switching member 22 can be inserted and installed even automatically and through self-actuation during the assembly. Preferred, however, is a guiding length 54 of the guiding pin 50 that is twice as long as the length 71 of the sealing section 48. In this way, even at the extreme front-most position of the switching member 22, a guiding of same between the fixed guiding links 51, that is in the guiding path 49 in the housing 18, can be attained.

After the switching member 22 has passed through the supporting ring 26 into the open space 36 and then into the reception chamber 62, the injection medium can, as is schematically indicated by the arrow 73, pass through the channels 52, past the guiding lugs 55, and up to the supporting ring 26. If a slight forward feeding force, or even none at all, is now applied in the direction of the arrow 67, the supporting ring 26, since the diameter 34 of the opening 33 is smaller than an outside diameter 74 of the guiding pin 50, lies against the latter, and a sealed closure is attained between the guiding pin 50 and the supporting ring 26, or more specifically, the sealing membrane formed by the latter. If in contrast with that the force is increased in the direction of the arrow 67, the medium 53 then presses in the direction of the arrow 73 from the inside towards the inner surface 29 of the supporting ring 26, as a result of which the sealing membrane is expanded or extended, and the medium 53 can pass through at the sealing membrane 48 along through the guiding channels 63 and into the injection needle 6.

If the injection medium is then expressed from the inner chamber 3 of the injection cylinder 2, and if an attempt is made to draw up a new injection medium—independently of whether or not the inner chamber 3 has now been completely emptied—then as a result of the lower pressure exerted by means of the piston 4, in conjunction with the elastic pre-stressing of the sealing member that is formed by the supporting ring 26, an immediate sealing closure is achieved between the supporting ring 26 and its face surface 75, so that a sealed closure is achieved even in the event of a pressure filling by means of which an additional injection medium is to be pressed through the injection needle 6 and into the inner chamber 3 of the injection cylinder 2.

If the lower pressure or the force introduced through the injection needle 6 of an additional injection medium becomes even higher, the switching member 22 is drawn back in the direction of the arrow 65, and specifically, to the extent that the surface 56 of the part of the switching member that is designed as a calotte shell section lies against the face surface 75 of the supporting ring 26. For that purpose the face surface 75 is designed expanding conically in the direction of the injection needle 6, in conjunction with which a side edge 76 of the cone runs parallel to a straight line 77, which extends at an angle 78 of 90° to a region that runs along the contact area between the face surface 75 and the calotte shell section of the surface 56. Thus, the face surface 75 forms a tangent surface to the calotte shell section, and thus an exactly sealing closure is achieved between the supporting ring 26, which is designed as a sealing membrane, and the sealing section 48.

As a result of this configuration of the face surface 75, even if there is a further increase in the pressure, in particular, even by means of the implementation of the surface 56 as a surface shaped like a calotte shell or, for example, as a truncated cone expanding in the direction of the injection needle or some kind of similar spatial configuration, no spreading force is applied to the supporting ring 26 in a radial direction, and as a result, any expansion of the sealing membrane or the supporting ring 26 for a movement of the switching member 22 in the direction of the arrow 65 is reliably prevented.

Figure 6:
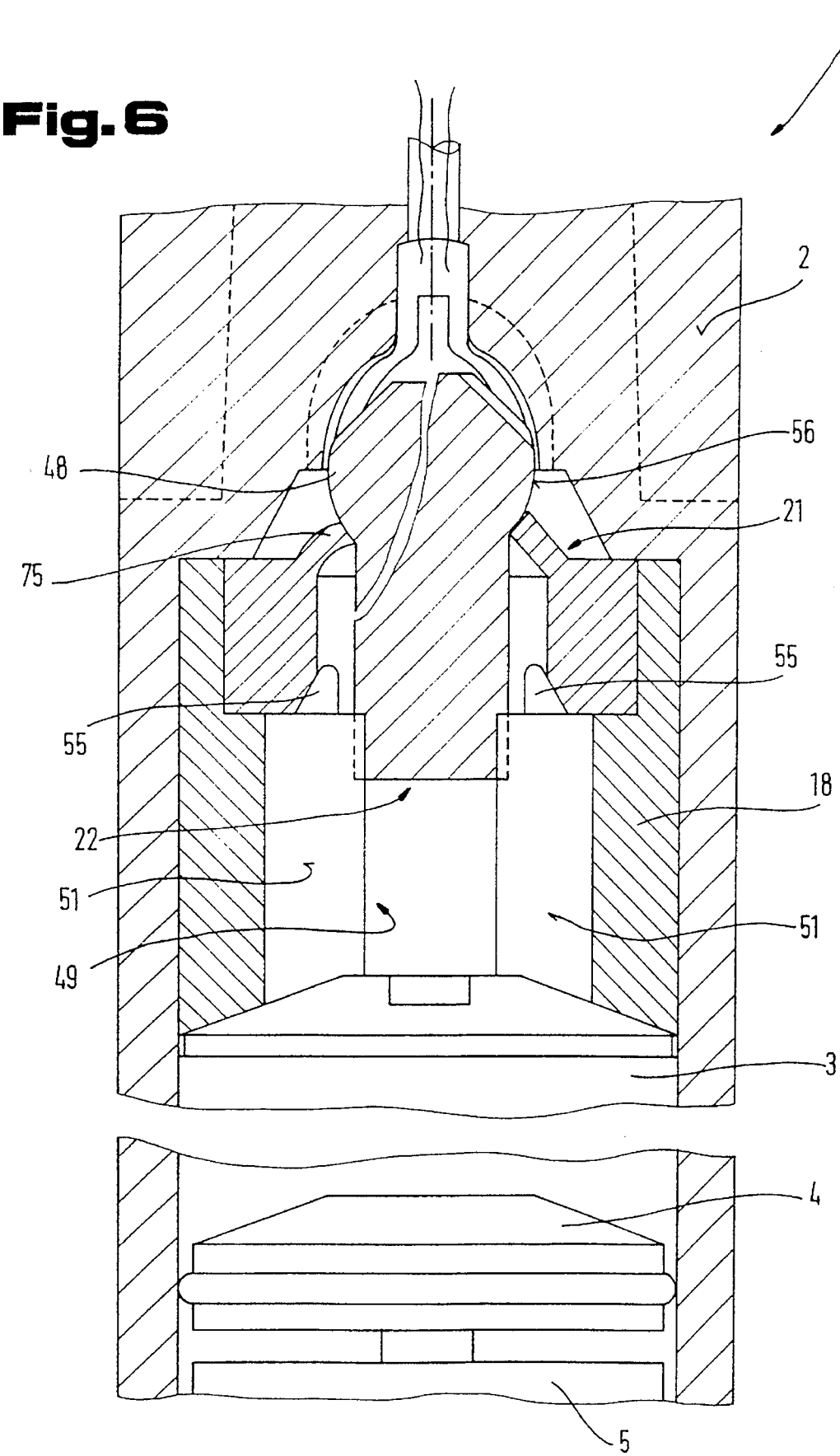
FIG. 6 the injection device in accordance with FIGS. 2 through 5 during an attempt, following the expression of a medium, again to draw up into the inner chamber of the injection cylinder a medium for a new injection.

This "sealing position" in the locking position of the switching member 22, in which the surface 56 lies against the face surface 75 of the sealing membrane, is shown in FIG. 6.

In the left half of this representation in FIG. 6, it is also shown that in the event of undue force being exerted on the switching member 22 from the direction of the injection needle 6—such as that which can occur during a pressure filling—by means of the use of an elastomer for the manufacture of the sealing membrane, or more specifically, the supporting ring 26, the supporting ring 26 deforms into a cuff-like shape, and thus there is built up in the sealing membrane and directed towards the longitudinal axis 28 a pre-stress force that leads to an even more secure sealing closure between the sealing membrane or the face surface 75, and the transition region from the guiding pin 50 to the sealing section 48.

Figure 7:
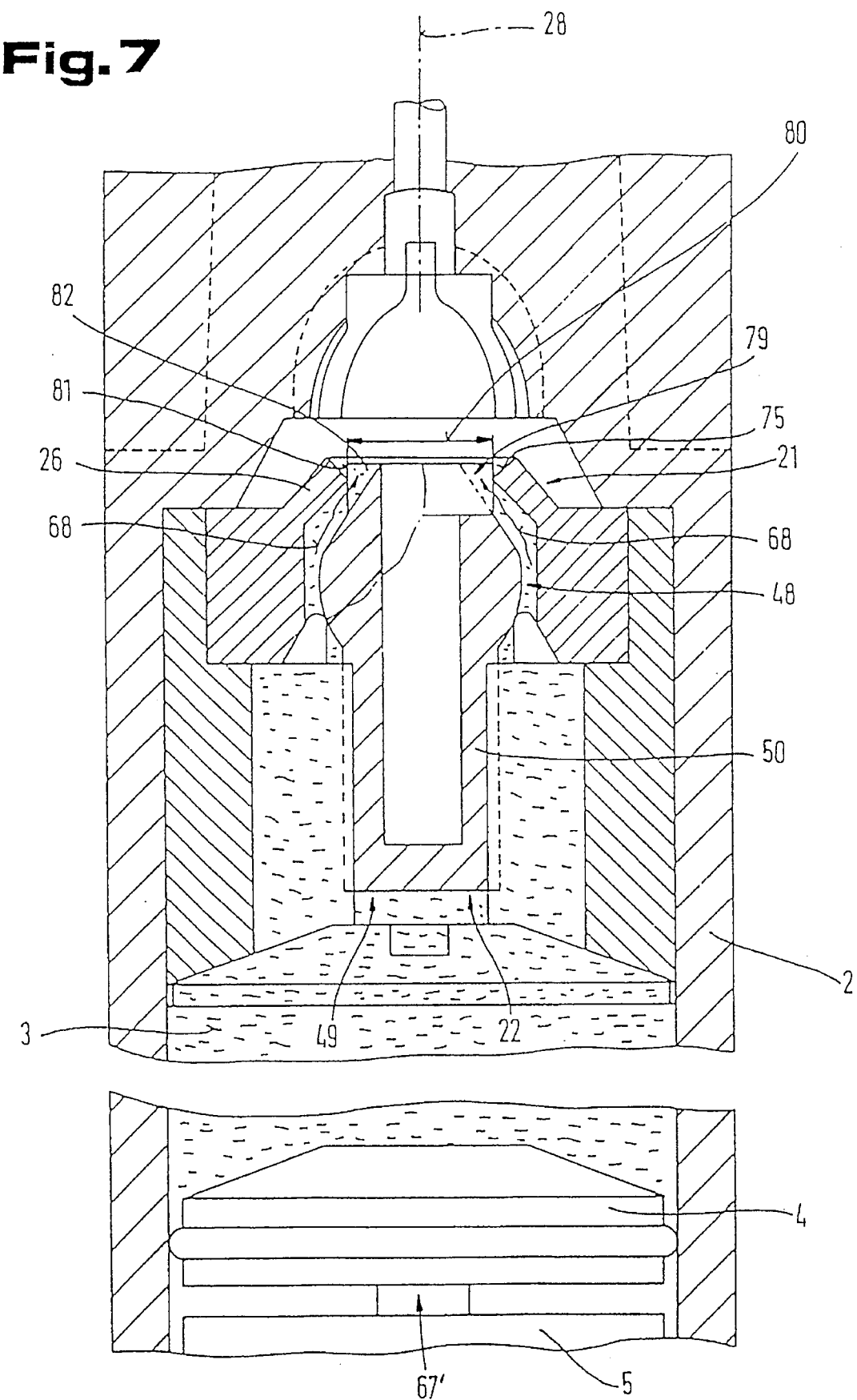
FIG. 7 a different form of implementation of an injection device in accordance with the invention with a sealing projection formed onto the sealing section, shown in a cross section side view.

In FIG. 7 an additional implementation variant is shown for the switching member 22 and the guiding pin 50. In this case, in union with the sealing section 48 there is provided a sealing projection 79, which exhibits an outside diameter 80 that is slightly greater than the inside diameter 34 of the opening 33 in the supporting ring 26, which acts as a sealing membrane and is shown in an unstressed state in FIG. 2. This brings about the fact that the opening 33 as shown with solid lines is expanded slightly in comparison with the rest position, which is shown with dashed lines in FIG. 7 and with solid lines in FIG. 2, and the face surface 75 lies with its inner edge sealing against an outside circumferential surface 81 of the sealing projection 79. As a result of this, in conjunction with the guiding of the guiding pin 50 in the guiding path 49, a centered support is ensured for the supporting ring 26, which! is made of an elastomer or an easily deformed material, even during storage and transport.

However, this orientation of the sealing membrane or the sealed closure between the supporting ring 26 and the sealing projection 79 also brings about the fact that when the injection medium is expressed from the inner chamber 3 of the injection cylinder 2 by means of the piston 4 via the piston rod 5, as a result of the small penetration surface area and in correspondence with the arrows 67', an additional forward feeding force is exerted on the switching member 22, so that during the expression of the medium 53, a reliable switching of the switching member 22 from the rest position shown in solid lines into the locking position shown in dashed lines is achieved.

In conjunction with this, however, in order to make possible the drawing up of the injection medium, at least one passage channel 82 that runs parallel to the longitudinal axis 28 is to be provided in the circumferential surface 81, so that when the injection medium is drawn up into the inner chamber 3, it can flow in with no problem.

Figure 8:
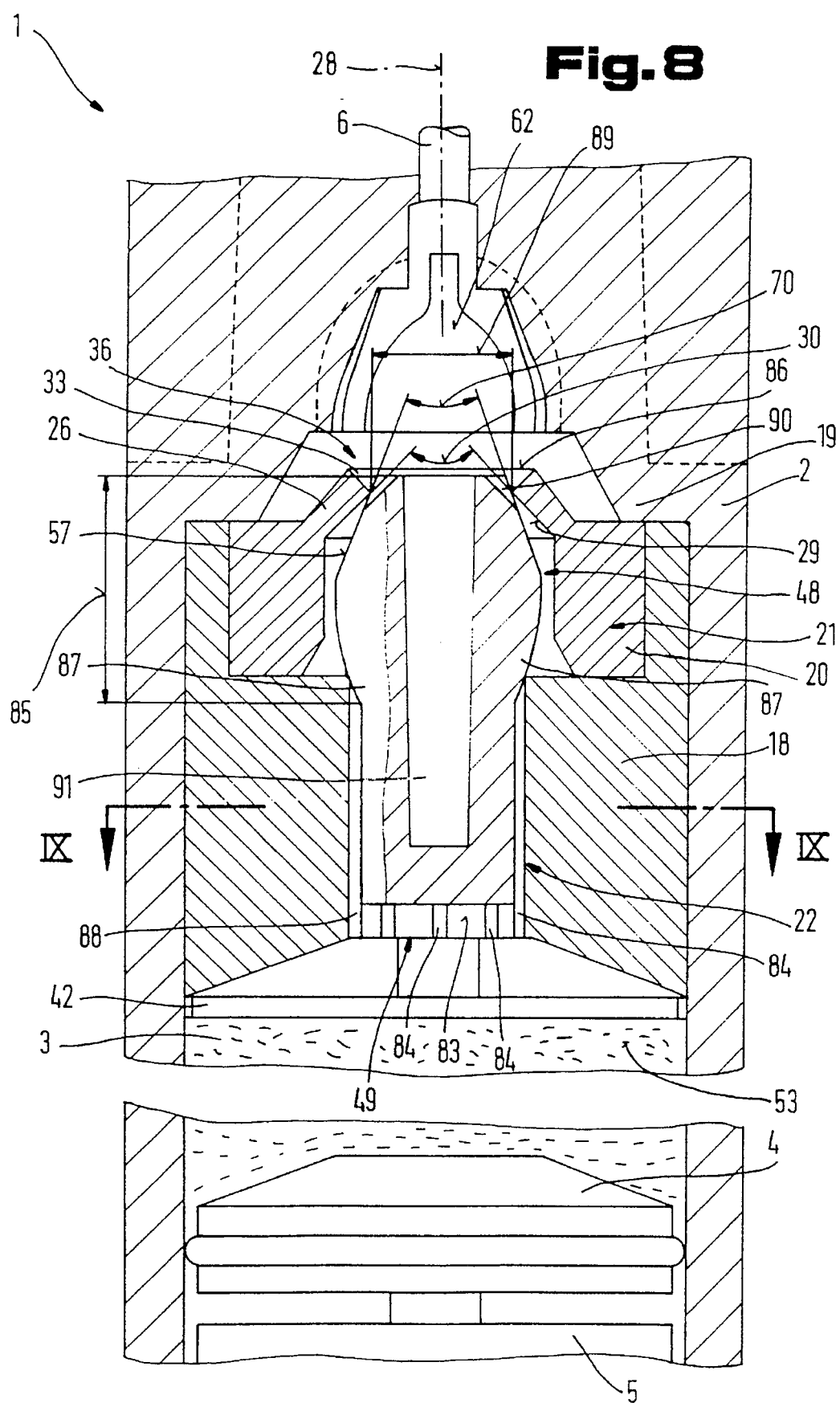
FIG. 8 a different implementation variant of the switching member with a sealing projection that protrudes beyond the sealing section in the direction of the injection needle, shown in a cross section side view.

In FIGS. 8 and 9 there is shown an implementation variant of the injection device 1 in which all of the parts that correspond with those described in the implementation example in accordance with FIGS. 1 through 7 have been assigned the same reference numbers.

The injection device 1 again includes an injection cylinder 2, in the inner chamber 3 of which a piston 4 can be displaced by means of a piston rod 5. Between the projections 19 and the limit stop part 42, there is shown a housing 18 for holding a retaining member 21, which, as in the previously described implementation variants, is produced by means of a disk 20 that is made from an elastomer, that is, from a material that can stretch and return elastically, in particular, a plastic or a pharmacological rubber or a silicon caoutchouc, in particular, with a Shore A hardness of from 40 to 65. For its part, the housing 18 is made from a plastic that is hard, stiff at room temperature, and can guide exactly.

A supporting ring 26 that is used as a sealing membrane can deform freely into an open space 36 in order to make possible the passing of a switching member 22 from the rest position shown in solid lines into a locking position that is located in the open space 36 or more specifically, in a reception chamber 62.

When compared to the previously described implementation variants, the switching member 22 is designed differently in the region of the sealing section 48. The switching member 22 is supported by means of its guiding element 23 in an exactly guided longitudinally displaceable manner in a guiding path 49 that is formed by a guiding bore 83. The tolerances between the guiding element 23 and the guiding path 49 are very small in order to prevent the canting or tipping of the switching member 22 into a position that is at an angle to the longitudinal axis 28. Distributed around the perimeter of the guiding bore 83 are channels 84, which are formed by grooves, for the flowing of the medium 53 from the inner chamber 3 into the injection needle 6 and from the injection needle 6 into the inner chamber 3.

These channels 84 can be placed with a separation of 90°, or with any other desired separation, so that depending on the quantity of liquid that is to flow through, sufficient passage cross-section is available for the medium 53.

In order to make possible a constantly centered retention of the elastically deformable soft sealing membrane, that is, the supporting ring 26, the sealing section 48 exhibits a length 85 that approximately corresponds to the distance between the end of the guiding path 49 and a face edge 86 of the supporting ring 26 that faces the injection needle 6.

Above all, the opening angle 70 of the conical section of the sealing member 48 that forms the surface 57 is selected to be smaller than an opening angle 30 of the inner surfaces 29 of the supporting ring 26.

In conjunction with this, it is also to be taken into consideration that in the arrangement in which retaining ribs 87 are placed in the transition region between the sealing section 48 and the guiding pin 50, and preferably lie on the webs 88 remaining between the channels 84, a diameter 89 of the sealing section 48, which is in the form of a truncated cone, corresponds to the diameter 34 of the supporting ring 26 in the rest position—as is shown in FIG. 2, for example. In this way, a sealing contact of the sealing section is achieved against the supporting ring 26 that forms the sealing membrane, or more specifically, against its inner edge. With the creation of a lower pressure in the inner chamber 3 for the purpose of drawing up the medium 53 into the inner chamber 3, by means of the piston 4 for example, in order to make possible a flowing of the medium between the switching member 22 and the sealing membrane, one or more pass-through channels 90, which can also be used simultaneously for de-airing, can be provided at the perimeter of the sealing section.

However, in each case care should be taken that the cross-section of the pass-through channel 90, or the total of the cross-sections, does not become so high that so much medium 53 can pass through them, for example, during expression of the same between the supporting ring 26 and the switching member 22 by means of the piston 4, that the remaining pressure from the pressurizing medium is no longer sufficient for pressing the switching member 22 through the supporting ring 26 and into the locking position.

The advantage of this solution lies in the fact that a pressure filling is made additionally difficult, since the injection device 1 exhibits a sealed closure between the injection needle 6 and the inner chamber 3 even in its unused state, and in addition, the opening 33 of the membrane, or more specifically, of the supporting ring 26 is always centered exactly on the longitudinal axis 28.

As can also be seen from this representation, the retaining ribs 87 can be provided in place of the guiding lugs 55 for the positioning of the switching member 22 relative to the position in the direction of the longitudinal axis 28, primarily in the rest position or during the drawing up of the medium 53, in order to ensure a sufficient pass-through cross-section for the passing through of the medium 53 between the sealing section 48 and the disk 20 into the channels 84. It can be seen in FIG. 9 that the channels 84 are placed around the entire perimeter of the guiding bore 83. Particularly for reasons of production by means of the injection molding process, the switching member 22 can be provided with a core recess 91 in order to attain a greater degree of stiffness because of the tubular configuration of the switching member that this causes, and to achieve a better cooling behavior of the injection molded part at the same time.

An additional advantage of the use of a hard plastic for the housing 18 and the switching member 22 lies primarily in the fact that the friction resistance of that type of hard plastic is significantly lower, and as a result, the force that has to be applied to move the switching member 22 from its rest position into its locking position, independently of the deformation resistance of the supporting ring and the sealing membrane, can be kept low. Above all, a significant advantage of the described implementation variants for the switching member 22 lies in the fact that it is in a frictional relationship only with the elastomer, that is, with the material that can be easily deformed elastically, in the area of the penetration through the sup- porting ring 26 that acts as a sealing membrane, and is free of this in the other areas, even the areas of the disk 20 that are adjacent to the support ring 26, so that here as well, no unnecessary increase in the frictional force, that is, no frictional resistance, can arise.

Above all, then, it is advantageous to use plastics with good sliding characteristics for the housing 18, independently of whether it is made up of one or several housing parts, and for the switching member 22, so that the amount of force necessary for the activation of the switching organ 22 for displacement from its rest position into its locking position can be kept as low as possible, and sufficiency can be found in the operating forces of 5N to 10N that are usual for the operation of hypodermic syringes and that are specified in part by means of standards as well.

In FIGS. 10 and 11, the housing 18 is shown as a single part. The exact design of the fixed guiding links 51 and the channels 52 is to be taken from this representation. As a result of the fact that via the channels 52 a broad, tangential incoming flow towards the surface 56 that is designed with a calotte shell shape is achieved, the penetration of the switching member is encouraged when a pressure is exerted on the medium 53 by means of the piston 4. At the same time, however, as a result of the precise carrying out of the guiding path 49 in the region of the fixed guiding links 51, a precise and tip-proof, guiding of the switching member 22 is ensured.

In addition, in FIG. 11 in particular, the recess 46 can be seen, in which the retaining member 21 can be placed, as can the guiding lugs 55 for centering the disk 20 of the retaining member 21 and for positioning the switching member 22 in the rest position.

In FIGS. 12 through 19, an implementation variant of an injection device 1 in accordance with the invention is shown. The FIGS. 13 through 16 differ from FIG. 12 only in that in FIG. 12, the position of the anti-reuse device 7 during the drawing up of a medium 53 from an ampoule 92 is shown, while in FIG. 13 the position for de-airing is shown, that is, for removing air bubbles 93 from the medium before the injection of the medium 53 into the body of a patient.

FIG. 14 shows the position of the anti-reuse device 7 during expression of the medium 53 into the body 94 of a patient, while FIG. 15 shows the position of the anti-reuse device 7 during an attempt to draw an additional injection medium from an ampoule 92 during the expression of the injection medium.

In FIG. 16 an additional possibility is shown for the way in which aspiration can be carried out with the injection device 1 shown in FIGS. 12 through 19, independently of a sufficient elasticity of the sealing membrane or more specifically, the supporting ring 26.

Since a number of the parts of the present injection device 1 match the parts of the previously described injection devices 1, the same reference numbers will be used for the parts to be described now that were used previously for parts of the same type. The injection device 1 again consists of an injection cylinder 2 with an inner chamber 3 in which the medium 53 to be injected is placed between a piston 4 that is joined to a piston rod 5, and an injection needle 6.

Between the injection needle 6 and the inner chamber 3 of the injection cylinder 2 there is found an anti-reuse device 7, which again exhibits a switching member 22, which can take the various positions shown in FIGS. 12 through 16.

Unlike the implementation examples described earlier, however, the housing 18 is made of a housing part 95 and a housing part 96, that is, in two parts. The retaining member 21, which can be designed in the same way as was described earlier, again includes a disk 20 and the supporting ring 26 that acts as a sealing membrane.

The housing 18 is placed in the injection cylinder 2 in the outlet or inlet area 37 that faces the injection needle 6, and can, for example, if the injection cylinder is made of plastic, be welded or bonded to it, or it can be secured between a face wall 97 of the injection cylinder 2 and a limit stop part 42, which can be formed by means of a collar 44 that projects beyond an inner surface 43 of the injection cylinder 2.

The housing parts 95, 96, which form the housing 18, and the retaining member 21 can be welded or bonded together, following the insertion of the retaining member 21 and possibly the switching member 22, in a joining area in order to achieve an assembly-ready module. However, it is also possible for the housing parts 95, 96 and the retaining member 21 to be designed in such a way that they can be joined together by means of snap and/or latching connections.

Figure 13:
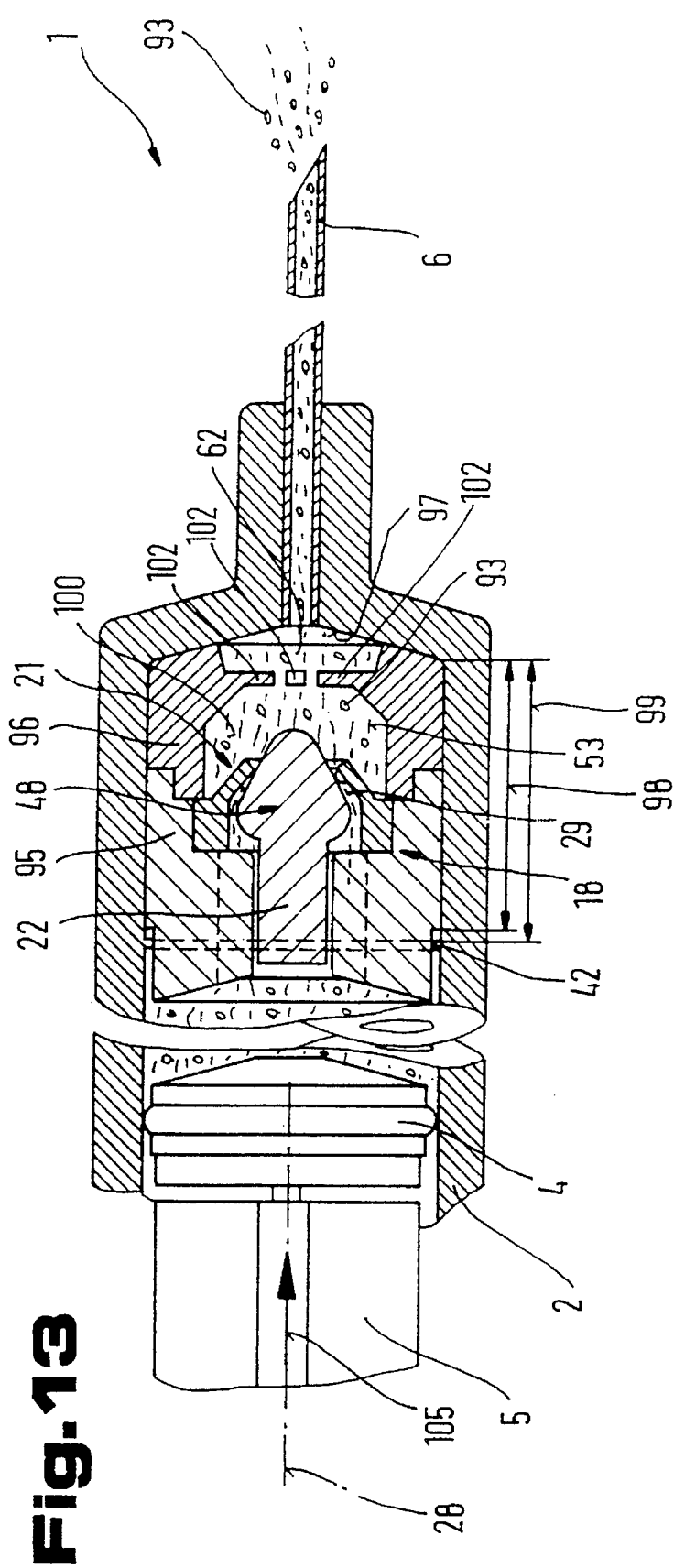
FIG. 13 the injection device in accordance with FIG. 12 in the position of the switching member for de-airing the inner chamber of the injection cylinder.

Thus it is also possible, as is shown in FIG. 13, for a guiding length 98 of the housing 18 to be smaller than a distance 99 between the face wall 97 and the limit stop part 42.

The exact function of this difference between the guiding length 98 and the distance 99 will be explained in more detail with the aid of the representation in FIG. 16.

The housing part 96, which is located between the retaining member 21 and the face wall 97 of the injection cylinder 2, exhibits the open space 36 that is needed for the expansion of the sealing membrane, specifically, the supporting ring 26 and that is designed in the direction of the injection needle 6 as resetting apparatus 100. This resetting apparatus 100 includes resetting arms 102 that are distributed around the perimeter of a pass-through opening 101 at a distance and that are designed as spring arms and can be elastically deformable. By means of the resetting behavior or the so-called memory effect that corresponds to the particular plastic material selected, after each deformation of the resetting arms 102 in the direction of the injection needle 6, and as a result of the pressing forward of the switching member 22 caused by the hydraulic pressure, a corresponding resetting spring force is created, which acts to cause a resetting of the switching member 22 into its original position, that is, into a sealing position against the supporting ring 26, immediately after the interruption of the force of pressure.

Between the resetting arms 102 and the injection needle 6, there can also be placed ahead of the face wall 97 a reception chamber 62, so that a corresponding open space is available for the elastic deformation of the resetting arms 102.

While the way in which the medium 53 can be drawn from an ampoule 92 is shown in FIG. 12, in FIG. 13 the de-airing of the injection device 1 is shown. In this case, in order to prevent a premature triggering or activation of the switching member 22, there is provided on an inner surface 29 of the retaining member 211a raised part 103, formed by a knob, for example, in the shape of a button of an elongated collar or something similar, running parallel to the longitudinal axis 28, for example. If a pressure is exerted that is smaller than the expression of the injection medium and that is shown in comparison with the full expression pressure, which is symbolized in FIG. 14 by means of a thick arrow 104, by means of a thinner arrow 105 in FIG. 13, and if the injection cylinder 2 is vibrated, that is, the injection device 1 is shaken, the air bubbles 93 that are contained in the medium 53, as is indicated schematically, then go through the injection needle 6 and to the outside, since unlike the liquid, for which the pass-through cross-section between the supporting ring 26 and the switching member 22 in the region of the sealing section 48 is too small, the air occlusions or air bubbles 93 can pass through.

Once the medium 53 in the injection device 1 has been de-aired, by means of the exertion of the maximum full feed force, which in accordance with the requirements in the standards should amount to between 7.5N and 10N, the medium 53 should be injected into the body 94 of a patient. By means of the force of pressure exerted by the user on the medium 53 via the piston 4 and the piston rod 5, the switching member 22 is pressed all the way through the supporting ring 26, which acts as a sealing membrane, and into the position shown in FIG. 14, until it comes to lie against the resetting arms 102 of the resetting apparatus 100, whereupon, if the force of pressure is sufficient, the resetting arms 102 are elastically deformed while developing a resetting force.

As soon as a force of pressure in accordance with the arrow 104 is exerted on the piston 4, the supporting ring 26, which acts as a sealing membrane, inflates and the medium 53 can enter between the switching member 22 and the supporting ring 26 of the retaining member 21 and between the resetting arms 102 into the injection needle 6, and from there into the body 94 of the patient.

With each interruption of the injection process, the retaining member 22 is pressed against the effect of the expression force and back against the supporting ring 26, or more specifically, against its encircling face surface 75, by the resetting arms 102 and the resetting force that has been developed in them. As a result of this, a sure sealing of the inner chamber 3 from the outside is ensured, so that the drawing up or pressing in of an additional medium following the first administration of a medium 53 is reliably prevented.

It is shown in FIG. 15 that as a result of the formation, tapering in the direction of the injection needle 6, of the supporting ring 26, the latter seats firmly against the side of the switching member 22, or more specifically, of the sealing section 48, that faces the guiding element 23, and a resetting force is exerted by the resetting arms 102 in the direction of the arrow 106 that is large enough so that a tight seal arises between the sealing section 48 and the supporting ring 26.

Finally, in FIG. 16 there is shown the way in which aspiration can be carried out with the described injection device 1. Namely, if first a small quantity of a medium 53 is administered into the body 94 of a patient, a lower pressure can be created by the piston 4 in the inner chamber 3 of the injection cylinder 2 by means of the drawing back the piston rod 5 in the direction of the arrow 106. As a result of the fact that the guiding length 98 is smaller than the distance 99, this brings about the fact that the entire housing 18, consisting of the two housing parts 95 and 96 which can be either bonded to each other or joined with each other by means of a welding process or a snap or pressure connection, is drawn back over the distance between the guiding length 98 and the distance 99 in the direction of the piston 4 until it lies against the limit stop part 42.

The volume that results in the inner chamber 3 of the injection cylinder 2 from the stroke and the cross-sectional area can now be used for drawing up into the injection cylinder 2 a volume resulting from a needle length 108 and an inside diameter 109 of the injection needle 6, in conjunction with which, the volume to be drawn up is preferably slighter larger than the volume resulting from the needle volume.

If, following the injection of a small quantity of the injection medium, the piston 4 is now drawn back until the housing 18 lies against the limit stop part 42, it can be determined whether blood is contained in the quantity of liquid that was drawn back so that a proper aspiration procedure can be carried out.

What is essential in conjunction with this is the fact that the anti-reuse device 7 is not triggered during this aspiration procedure, so that in the event that the doctor has struck a vein during the insertion, the aspiration procedure can be repeated once again before the medium 53 is fully administered into the body 94 of the patient.

What is essential in conjunction with this is the fact that by means of a possible design of that type, which is in no way absolutely necessary, however, it is also possible to carry out the aspiration procedure even if the anti-reuse device 7 has been triggered and the switching member 22 has been moved from its rest position into the locking position. In spite of that, it is also ensured that as a result of the sealing of the switching member 22, no medium 53 can be drawn up into the inner chamber 3 of the injection cylinder 2 during the aspiration procedure.

Shown in FIGS. 17 through 19 are sections through various regions of the injection device 1.

Thus in FIG. 17, the exact arrangement and distribution of the resetting arms 102 of the resetting apparatus 100 is shown. In the case of the present implementation example, four resetting arms 102 distributed around the perimeter are being used. However, it is also possible to find sufficiency in only one or two resetting arms, or also to provide more than four resetting arms.

The representation in FIG. 18 shows the overlapping and arrangement of the housing parts 95 and 96, as well as the supporting ring 26 of the retaining member 21 in the contact region of the supporting ring 26, which forms that sealing membrane, at the sealing section 48 of the switching member 22.

In FIG. 19 it can be seen that the guiding element 23 is guided between fixed guiding links 51 of the housing part 95, which form between them channels 52 for the passing through of the medium 53 parallel to the guiding element 23, so that a tangential incoming flow is also possible over cross-section of the sealing element 48 that projects beyond the perimeter of the guiding element 23.

The arrangement and spatial design of the sealing section 48 can be changed as desired in order to match it to the desired implementation variant within the framework of the previously described implementation variants and the implementation variants described in the following. Primarily, it is also possible that in place of the calotte shell design in the region of the switching member 22 surface that is facing the guiding element 23, a conical configuration is possible as well.

Figure 20:
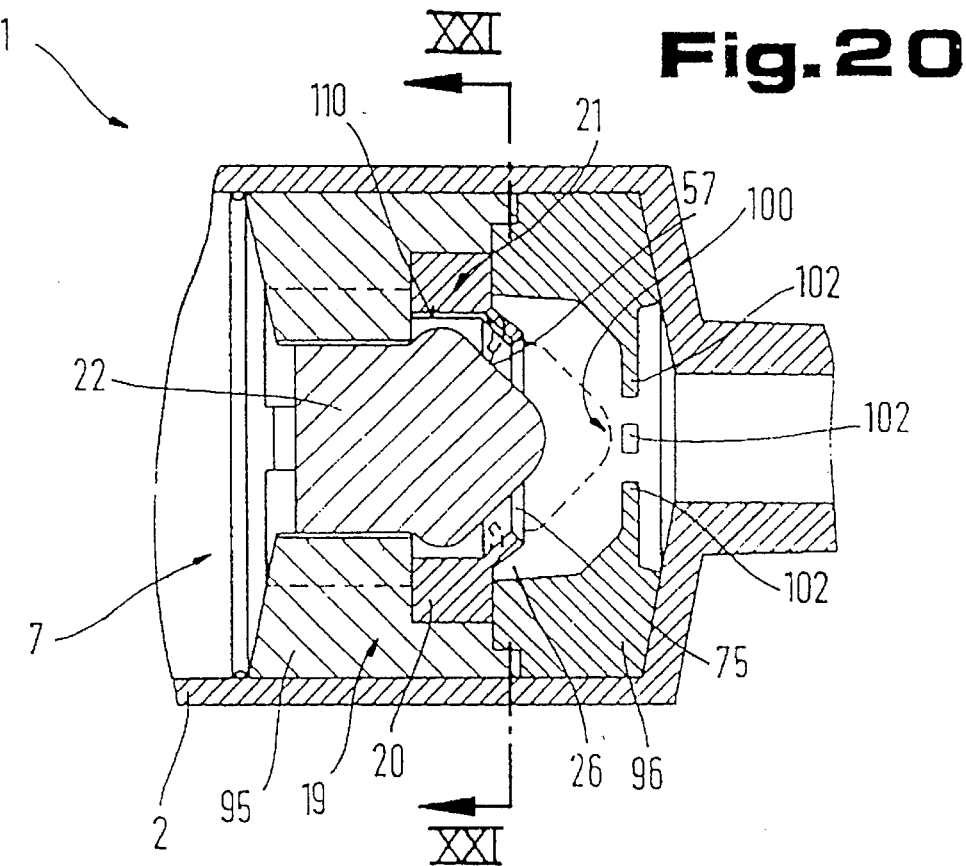
FIG. 20 a different design of an injection device in accordance with the invention, with a different implementation variant of a de-airing channel, in a cross section side view, with a reception space placed in the front end region of the injection cylinder for the switching member.
Figure 21:
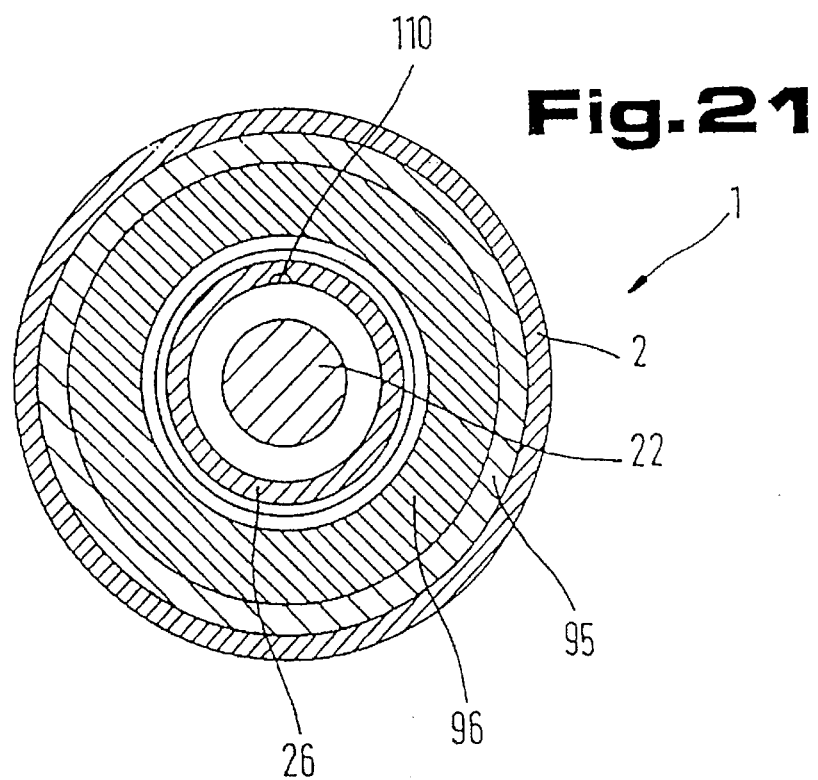
FIG. 21 the injection device in accordance with FIG. 20, in front view, a cross section in accordance with the lines XXI—XXI in FIG. 20.

In FIGS. 20 and 21 there is shown a part of the injection device in accordance with FIGS. 12 through 19, in a larger scale and with slight changes versus the previously described form of implementation.

Primarily shown in FIG. 20 is only that part of the injection device 1 in which the anti-reuse device 7 is placed. It can be seen from this that the housing 18 is made up of two housing parts 95, 96, between which the retaining member 21, and in particular, the disk 20 with the support ring 26, is placed. The housing part 95 also includes as an integrated component the resetting apparatus 100 with the resetting arms 102, which are elastically deformable in the direction of movement of the switching member 22.

In order to make possible a de-airing of the medium 53 that is present in the inner chamber 3 of the injection cylinder 2 when the switching member 22 is lying with its surface 57 at the supporting ring 26, a de-airing channel 110 is now placed above the headway of the retaining member 21.

For the layout of this de-airing channel 110, it is of course also possible for a number of channels of that type to be placed distributed around the perimeter of the retaining member 21, and the same criteria apply as for the arrangement of the de-airing channels 60 described in FIG. 2. They must be designed in such a way in terms of their cross-section and their course, that they only allow the passage of air, but under no circumstances a passing through of a medium 53.

Figure 22:
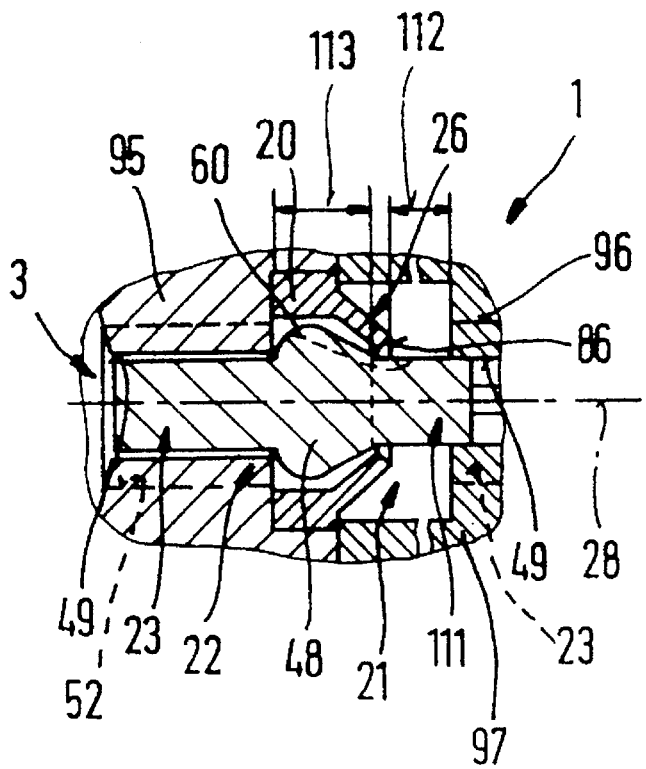
FIG. 22 a part of a different implementation variant of an injection device in accordance with the invention, in the region of the anti-reuse device, shown in a cross section side view.
Figure 23:
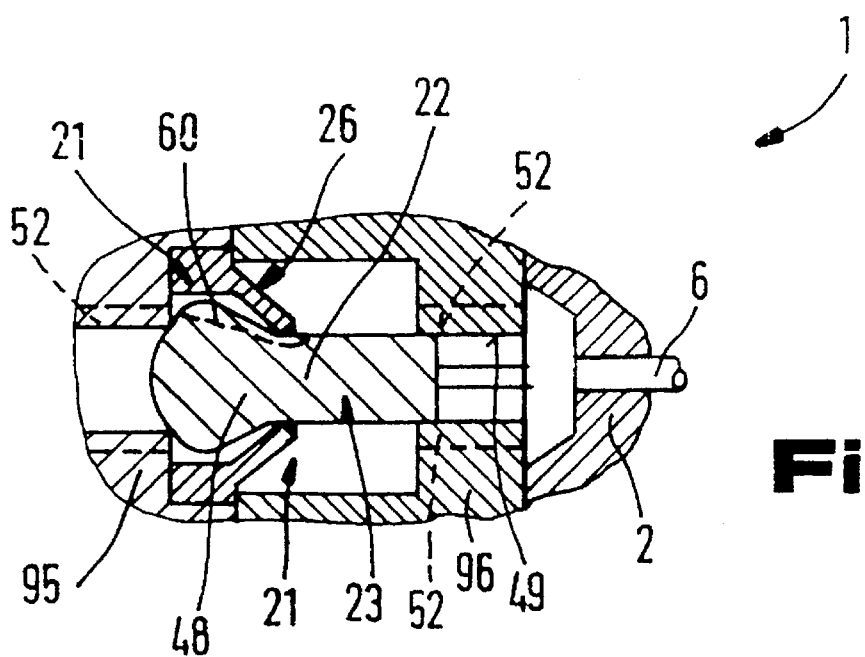
FIG. 23 a part of a different implementation variant of an injection device in accordance with the invention, in the region of the switching device, shown in a cross section side view.

In FIGS. 22 and 23, then, additional implementation variants are shown for the guiding of the switching member 22 and the arrangement of the guiding path 49.

Thus, in the case of the implementation example in FIG. 22, the sealing section 48 of the switching member 22 is joined in the region of both end faces with a guiding element 23 and 111.

By virtue of the fact that guiding elements 23 and 111 are now provided on both sides of the sealing section 48, and to each of these guiding elements 23 and 111 there is allocated in the corresponding housing part 95 and 96 its own guiding path 49, an exactly centered movement of the switching member 22 along, that is, parallel to, the longitudinal axis 28 is possible. As a result of that, sufficiency can be found for the guiding elements 23 and 111 even with relatively short guiding lengths, since a tipping of the switching member 22 is primarily prevented during the passage through the retaining member 21. In order to make possible fault-free functioning and a sure passing of the sealing section 48 through the retaining member 21, a distance 112 is to be selected that is equal to or greater than a spacing 113. In conjunction with this, the spacing 113 extends between the transition region between the guiding element 23 and the sealing section 48 on the one hand, and the transition area between the sealing section 48 and the guiding element 111 on the other. Both the distance 112 as well as the spacing 113 are determined parallel to the longitudinal axis 28 of the injection device 1. In order to make possible an unhindered flow of the medium 53 past the guiding elements 23 and 111, channels 52 can again be placed in the region of the guiding element 23, as well as channels arranged in approximately the same way in the region of the guiding element 111.

In order to make possible a fault-free de-airing of the inner chamber 3 of the injection cylinder 2 with this injection device 1 in accordance with FIG. 22 as well, there can be placed in the region of the sealing section 48 to the region of the guiding element 111 a de-airing channel 60.

The implementation example shown in FIG. 23 differs from the variant shown in FIG. 22 only by virtue of the fact that exclusively in the housing part 96, that is, that one which is placed lying closer to the injection needle 6, there is placed a guiding path 49, and that in the rest position, only the sealing section 48 of the switching member 22 is found on the other side of the supporting ring 26 of the retaining member 21. This form of implementation has the advantage that the entire surface of the sealing section is available on the side facing the piston 4 for the exerting of a force of pressure for the pressing through of the sealing section during the switch from a rest position into a locking position, and the certainty of the triggering of the switching member 22 can be increased in this way.

Also advantageous with this form of implementation, however, is the fact that the sealing element, that is, the supporting ring 26 of the retaining member 21, can support itself in a centered manner on the guiding element 111 for the entire duration of use of the injection device 1, as a result of which, an appropriately tight seal between the supporting ring 26 and the allocated guiding elements 23, 111 or the sealing section 48 can be attained, even in the various positions. Naturally, a de-airing channel 60 can be placed in the perimeter surface of the sealing section 48 in the region of the supporting ring 26 with this implementation variant of the injection device 1 as well.

Preferably, an overlapping of the guiding elements 23, 111 and the guiding path 49 should amount to between 0.8 and 1.5 times the diameter of the guiding element 23, 111, especially if a guiding element 23 or 111 is placed on only one side of the sealing section. Basically, however, the minimum overlap between the guiding element 23 or 111 and the guiding path 49 should be established based on the maximum permissible tipping tolerance, or more specifically, the maximum permissible tipping angle. The smaller the tolerance for the tipping angle is, the longer should be the selected overlap between the guiding element 23 or 111 and the guiding path 49. Added to that, however, is the fact that with a smaller dimensional tolerance in the diameter dimensions of the guiding element 23 or 111 and the guiding element 49, this overlap length can be selected smaller than with higher tolerances, that is, less exact fits. In conjunction with this, it is advantageous if the play between the guiding element 23 or 111 and the guiding path 49 is in the range between 0.01 mm and 0.05 mm, that is, a fit or more specifically, a close fit with limited tolerances, in order to reliably prevent a tipping or angled positioning of the switching member 22 in the guiding path 49.

In principle, in all of the previously described implementation examples, care should be taken that channels 52 and 84 that are placed in the region of the guiding path 49 in a preferred implementation example exhibit in total a cross-sectional area that is equal to or less than the cross-sectional area of the face 68 of the switching organ 22 that is facing the piston 4.

Specifically, the greater the cross-sectional area of the channels 52 and 84 is, the higher is the pressure loss that occurs during the flowing of the injection medium through these channels 52 and 84, and, especially in the case of liquids of low viscosity, this can lead to the fact that force exerted on the face 68 is no longer sufficient to move the switching member 22 through the retaining member 21, that is, to activate the anti-reuse device, in order to prevent any further use of the hypodermic syringe.

In conjunction with this, care should also be taken, even in the case of high viscosity liquids, or more specifically, injection media, that the proportion of the liquid quantity that flows past the switching member 22 to the side, that is, tangentially, not be too high, since this incoming cross-flow hinders the forward movement of the switching member 22 in the direction of the injection needle during the expression of the injection medium, and delays, and can therefore also counteract, the desired switching movement.

For this reason, it is therefore advantageous if the total cross-sectional areas of all of the channels 52 and 84 amounts to only about 40 and 70 percent of the cross-sectional area of the face 68.

In addition, by way of supplementing the implementations regarding the design of the channels 60 or the pass-through channels 90, with reference to the previous implementations, and specifically, to the implementation example shown in FIG. 2, among other places, as well as to the implementation example as it is shown in FIG. 8, the fact should be recorded that the cross-sectional area, that is, the open passage through these channels 60 and pass-through channels 90 in a preferred implementation example should be selected in such a way that a passing through of liquids is not possible or is possible in only the smallest possible amounts. Primarily, it is to be recommended that, for example, only such a channel 60 or pass-through channel 90 be placed that extends from the surface 56 to the region of a face surface 61 of the sealing section 48. In this case, this channel can be used only for the expression of air from the inner chamber between the switching member 22 and the piston 4, and an appropriate bypass channel is to be provided for the drawing up of a medication through the injection needle into this inner chamber. As a result Of this, in the designing of the cross-section and the cross-sectional area of this channel, no account needs to be taken of the incoming flow of the medium during its drawing up, and this channel 60 can be designed in accordance with the requirements for the de-airing of the injection medium.

Primarily, however, with a preferred implementation example care should be taken that the cross-sectional area of this channel amounts to only a fraction, that is, a range of from 0.1 to a maximum of 10 percent, of the cross-sectional area of the face 68 of the switching member 22, even if it is divided up among a number of channels 60 around the perimeter of the switching member 22, and that it is also ensured that no liquid can pass through these channels. The reason for this lies primarily in the fact that the force of pressure that arises by means of the pressing of the medium in between the switching member 22 and the retaining member 21 is not to become greater than the force necessary to press the switching member 22 through the retaining member 21, since otherwise the switching member 22 could be pressed from the retaining member 21 back in the direction of the piston 4 as a result of the force exerted on the medium by means of the piston 4, and thus the passing through of the injection medium could be made possible without the switching of the switching apparatus 22.

With that, the use of cross-sections of only 0.005 to 0.05 mm is to be recommended for channels of that type, depending upon the viscosity of the particular injection medium in question, with a smaller cross-section to be selected for a higher viscosity.

Finally, let it also be pointed out that, naturally, any desired choice of combinations and composition of the individual design variants is possible for the injection device in accordance with the invention, particularly for the housing 18, the retaining member 21, and the switching member 22, in conjunction with which, even the forms of implementation of those parts that are described in various implementation examples can be combined into an injection device in accordance with the invention. Individual parts of the previously described combination of features can also form separate, independent solutions in accordance with the invention.

| List of Reference Symbols | |
| --- | --- |
| 1 Injection device | 41 Inside diameter |
| 2 Injection cylinder | 42 Limit stop part |
| 3 Inner chamber | 43 inner surface |
| 4 Piston | 44 Collar |
| 5 Piston rod | 45 |
| 6 Injection needle | 46 Recess |
| 7 Anti-reuse device | 47 Face |
| 8 Stroke | 48 Sealing section |
| 9 Limit stop | 49 Guiding path |
| 10 Inner surface | 50 Guiding pin |
| 11 Height | 51 Fixed guiding links |
| 12 Piston ring | 52 Channel |
| 13 Piston body | 53 Medium |
| 14 Fixed link | 54 Guiding length |
| 15 Fixed link | 55 Guiding lug |

25
-continued

List of Reference Symbols

| | | | |
|---|---|---|---|
| 16 | Weakening location | 56 | Truncated cone |
| 17 | Needle projection | 57 | Surface |
| 18 | Housing | 58 | Diameter |
| 19 | Projection | 59 | Outside diameter |
| 20 | Disk | 60 | De-airing channel |
| 21 | Retaining member | 61 | Face surface |
| 22 | Switching member | 62 | Reception chamber |
| 23 | Guiding element | 63 | Guiding channel |
| 24 | Plasic | 64 | O-ring |
| 25 | Plastic | 65 | Arrow |
| 26 | Supporting ring | 66 | Arrow |
| 27 | Through-bore | 67 | Arrow |
| 28 | Longitudinal axis | 68 | Face |
| 29 | Inner surface | 69 | Arrow |
| 30 | Opening angle | 70 | Opening angle |
| 31 | Opening angle | 71 | Length |
| 32 | Outer surface | 72 | Total length |
| 33 | Opening | 73 | Arrow |
| 34 | Diameter | 74 | Outside diameter |
| 35 | Diameter | 75 | Face surface |
| 36 | Open space | 76 | Side edge |
| 37 | Inlet area | 77 | Straight line |
| 38 | Width | 78 | Angle |
| 39 | Limiting wall | 79 | Sealing projection |
| 40 | Outside diameter | 80 | Outside diameter |
| 81 | Outside perimeter surface | 121 | |
| 82 | Passage channel | 122 | |
| 83 | Guiding bore | 123 | |
| 84 | Channel | 124 | |
| 85 | Length | 125 | |
| 86 | Face edge | 126 | |
| 87 | Retaining rib | 127 | |
| 88 | Web | 128 | |
| 89 | Diameter | 129 | |
| 90 | Pass-through channel | 130 | |
| 91 | Core recess | 131 | |
| 92 | Ampoule | 132 | |
| 93 | Air bubble | 133 | |
| 94 | Body | 134 | |
| 95 | Housing part | 135 | |
| 96 | Housing part | 136 | |
| 97 | Face wall | 137 | |
| 98 | Guiding length | 138 | |
| 99 | Distance | 139 | |
| 100 | Resetting apparatus | 140 | |
| 101 | Pass-through opening | 141 | |
| 102 | Resetting arm | 142 | |
| 103 | Raised part | 143 | |
| 104 | Arrow | 144 | |
| 105 | Arrow | 145 | |
| 106 | Arrow | 146 | |
| 108 | Needle length | 148 | |
| 109 | Inside diameter | 149 | |
| 110 | De-airing channel | 150 | |
| 111 | Guiding element | 151 | |
| 112 | Distance | 152 | |
| 113 | Spacing | 153 | |
| 114 | Distance | 154 | |
| 115 | | 155 | |

We claim:

1. Single-use injection device comprising an injection cylinder for receiving a liquid medium, an inner chamber located inside the injection cylinder, an injection needle attached to the injection cylinder, an inlet area located adjacent to the injection needle, the injection device having a longitudinal axis which extends in the direction of the injection needle, a piston that can slide inside the injection cylinder and a piston rod, the piston being movably linked to the piston rod which extends in a direction opposite to the injection needle, and an anti-reuse device that is actuated by the medium moved by the piston and that is arranged in the inlet area of the injection cylinder, a ring-shaped retaining member having an opening, the ring-shaped retainer being located in the injection cylinder between the injection needle and the piston, the anti-reuse device including a switching member having a sealing section with a larger cross-sectional area than a passage cross-section of the opening in the ring-shaped retaining member, the sealing section being retained in a rest position by means of the ring-shaped retaining member which is elastically deformable in at least one of a radial direction and in a direction of the injection needle on the side of the ring-shaped retaining member that faces the piston, and the switching member can be moved from the rest position into a locking position wherein the sealing section is located on the side of the ring-shaped retaining member that faces the injection needle, the ring-shaped retaining member providing a sealing stop for the switching member in the direction of the piston, and that a reception area for at least the sealing section of the switching member is arranged between the ring-shaped retaining member and the injection needle, the ring-shaped retaining member (21) being made of an elastically restorable material and is held in position on a housing (18) of the anti-reuse device (7) that is set inside the inner chamber (3) of the injection cylinder (2) and is made of a harder material than the ring-shaped retaining member (21), the switching member (22) includes a guiding element (23) that is adjacent to the sealing section (48) that is moveable in a guiding path (49) located in the injection cylinder (2), a guiding length between the guiding element (23) and the guiding path (49) being longer than at least the distance between the rest and locking positions of the switching member (22).

2. Injection device in accordance with claim 1, wherein the guiding element (23) includes a guiding pin (50) that extends in the direction of the longitudinal axis (28) of the injection device (1), the switching member (22) having a total length (72) and the sealing section having a second length (71), the total length of the switching member being greater than twice the second length (71) of the sealing section (48).

3. Injection device in accordance with claim 2 wherein the guiding pin (50) has a first length and the sealing section (48) has a second length (71), the first length corresponds to a multiple of the second length (71).

4. Injection device in accordance with claim 2 wherein the guiding path comprises a guiding bore (83) which extends through the housing (18) in a longitudinal direction, the guiding pin (50) being guided in the guiding bore (83) longitudinally with low tolerance in the guiding bore (83).

5. Injection device in accordance with claim 4, characterized by the fact that channels (84) that are formed by groove-like indentations are located in the guiding bore (83) and extend parallel to the longitudinal axis (28) of the injection device (1), the channels being distributed around a perimeter of the guiding (83) bore at a distance from each other.

6. Injection device in accordance with claim 2, characterized by the fact that the sealing section (48) is formed by means of a calotte shell section which is adjacent to the guiding pin (50), the sealing section having an outside diameter (59) and the guiding pin having an outside diameter, the outside diameter of the sealing section being larger than the outside diameter (74) of the guiding pin (50), and an end part of the switching member (22) lying opposite the guiding pin (50) is formed by a truncated cone.

7. Injection device in accordance with claim 6, characterized by the fact that an opening angle (70) of the truncated cone (56) is 90° or smaller.

8. Injection device in accordance with claim 2, characterized by the fact that the sealing section (48) is formed by a calotte shell, the calotte shell having an outside diameter, the guiding pin having an outside diameter, and the opening

(33) of the ringed shaped retaining member having a diameter, the outside diameter (59) of the calotte shell being larger than the outside diameter (74) of the guiding pin (50), the sealing surface having a circular face surface (61) having a diameter (58) that is smaller than the outside diameter (74) of the guiding pin (50) and the diameter (34) of the opening (33) of the retaining member (21).

9. Injection device in accordance with claim 8, characterized by the fact that the diameter (34) of the opening (33) of the supporting ring (26) is smaller than the outside diameter (74) of the guiding pin (50).

10. Injection device in accordance with claim 8, characterized by the fact that the ring-shaped retaining member (21) includes a supporting ring (26) which has a cone envelope section that has a diameter (35) of a base circle, and the sealing section (48) has a maximum outside diameter (59), the diameter (35) of the cone envelope section being greater than the maximum outside diameter (59) of the sealing section (48) and of which the diameter (34) of the opening (33) is smaller than an outside diameter (59) of the sealing section (48).

11. Injection device in accordance with claim 10, wherein the supporting ring (26 has an inner surface (29) which faces the sealing section (48), and an opening angle (30) of the inner surface (29) of the supporting ring (26) that faces the sealing section (48) in the rest position is 90° or greater.

12. Injection device in accordance with claim 10, characterized by the fact that the supporting ring (26) is free both in the longitudinal direction of the injection device as well as in a radial direction relative to the injection cylinder (2).

13. Injection device in accordance with claim 10, characterized by the fact that at least the supporting ring (26) surrounding the opening (33) is made from an elastomer with a Shore A hardness of from 40 to 65.

14. Injection device in accordance with claim 10, characterized by the fact that the supporting ring (26) is made of an elastically extendable and restorable material.

15. Injection device in accordance claim 10, wherein the supporting ring (26) includes a face surface (75) which is aligned at least one of perpendicular and tangentially to the surface (57) of the sealing section (48) that is allocated to the guiding pin (50).

16. Injection device in accordance with claim 1, wherein the ring-shaped retaining member comprises a ring-shaped disk, the housing (18) is provided with a cylindrical recess (46) in an end area that faces the injection needle (6) for reception of the ring-shaped disk, a limit stop is located in the injection cylinder, and the housing includes a face (47), the face (47) of the housing (18) and the ring-shaped disk lie against the limit stop.

17. Injection device in accordance with claim 16, wherein the guiding path comprises a guiding bore (83) which extends through the housing (18) in a longitudinal direction, the housing includes a face wall that lies opposite to and faces the piston, and the guiding bore extends from the cylindrical recess (46) in the direction of the longitudinal axis (28) of the injection device (1) into an area of the face wall.

18. Injection device in accordance with claim 16, wherein the recess (46) has a diameter, and the ring-shaped retaining member (21) has an outside diameter, the diameter of the recess (46) corresponds to the outside diameter (40) of the retaining member (21), the housing (18) further comprises a ring-shaped projection (19) which has an inside diameter (41), and the diameter of the recess (46) is larger than the inside diameter (41) of the ring-shaped projection (19).

19. Injection device in accordance with claim 1, characterized by the fact that the housing (18) is made up of several housing parts (95, 96) and the ring-shaped retaining member (21) is inserted and held in position between at least two housing parts (95, 96).

20. Injection device in accordance claim 19, characterized by the fact that the housing parts (95, 96) are joined to each other by one of bonding, welding, ultrasonic welding, a snap connection and a pressure connection.

21. Injection device in accordance with claim 1, characterized by the fact that the injection cylinder (2) has a complementary form to the external form of at least the sealing section (48) of the switching member.

22. Injection device in accordance with claim 1, characterized by the fact that between the ring-shaped retaining member (21) and the injection needle (6) there is placed a resetting apparatus (100) that acts in the direction of the piston (4) comprising resetting arms (102), and a spacing is provided between the resetting arms (102) of the resetting apparatus (100) and the face surface (61) of the retaining member (21) parallel to the longitudinal axis (28) which is equal to or smaller than a length (71) of the sealing section (48).

23. Injection device in accordance with claim 22, characterized by the fact that the resetting arms (102) of the resetting apparatus (100) are spring arms and are elastically deformable.

24. Injection device in accordance with claim 22, wherein the ring-shaped retaining member (21) includes a face edge (86) and a spacing (113) is provided between the wall areas of the switching member (22) that are lying against the retaining member (21) and those lying against the resetting arms (102), and wherein the retaining member is movable to a deformed position under a maximum resetting force, and a distance (112) between the face edge (86) of the retaining member (21) in the deformed position under the maximum resetting force and the resetting arms (102) is greater than the spacing (113) between the wall areas of the switching member (22) that are lying against the retaining member (21) and those lying against the resetting arms (102).

25. Injection device in accordance with claim 1, wherein a propulsive force acts on the piston and the ring-shaped retaining member provides a retaining force in the direction of the injection needle (6) which is smaller than the propulsive force acting upon the piston (4).

26. Injection device in accordance with claim 1, wherein the injection cylinder has an inner chamber facing the injection needle, and a limit stop is located in a face wall of the inner chamber, one of the housing (18) and the retaining member (21) is held in the direction of the longitudinal axis (28) of the injection device between the limit stop located in the face wall (97), the limit stop comprising at least one limit stop part (42) projecting into the inner chamber (3).

27. Injection device in accordance with claim 26, a longitudinal distance is defined between the face wall (97) and the at least one limit stop part (42), the longitudinal distance being greater than an overall length of the housing (18).

28. Injection device in accordance with claim 1, wherein the injection cylinder has an inner chamber facing the injection needle and a needle channel is located between the needle and the inner chamber, the product of the difference between the longitudinal distance and the overall length of the housing (18) and the cross-sectional area arranged perpendicular to the longitudinal axis (28) is larger by 5 to 30% than the volume of the injection needle (6) and of the needle channel between the needle and the inner chamber (3) of the injection cylinder (2).

29. Injection device in accordance with claim 1, wherein the guiding element includes a face (68), the inner chamber faces the injection needle and a needle channel is located between the needle and the inner chamber, the injection needle includes a channel having a defined volume, the device having a total volume resulting from a product of the difference between a distance (99) and the guiding length (98), and the cross-sectional area of the face (68) of the guiding element is equal to or greater than the volume of the channel of the injection needle (6) and of the needle channel between the needle and the inner chamber (3) of the injection cylinder (2).

30. Injection device in accordance with claim 1, wherein a needle projection (17) is located in the injection cylinder (2), and the guiding path (49) for the guiding element is arranged in the needle projection (17) of the injection cylinder (2).

31. Injection device in accordance with claim 1, the injection cylinder (2) includes a face wall (97) in its one end region which closes off the injection cylinder, and its opposite end is open, the injection cylinder has an inner chamber facing the injection needle and a needle channel is located between the needle and the inner chamber, the retaining member (21) further including an opening (33), a piston rod (5) projects into the inner chamber (3) of the injection cylinder (2) from the open end such that the piston (4) can be pushed into the inner chamber (3) of the injection cylinder (2) as well as be withdrawn from it, and in conjunction with this the face wall (97) is penetrated by the needle channel and that against the face wall (97) there lies a housing (18) which is inserted into the inner chamber (3) of the injection cylinder (2), and which is set in a sealing fashion, by a sealing means, into the inner chamber (3) of the injection cylinder (2), and which includes one housing part on the needle side lying against the face wall (97) and one piston side housing part (95, 96), which preferably overlap each other, an opening is provided through the needle and piston side housing parts in the longitudinal direction, and the ring-shaped retaining member (21) is located between the piston (4) and the needle side housing part (96), the switching member comprising a cylindrical guiding pin (50) that is guided with little play in a bore located in one of the two housing parts (95, 96) and the injection cylinder (2), the switching member (22) including a tapering end on the face and a sealing section connected to the guide pin (50) the sealing section having a greater cross-sectional area than the opening (33) in a retaining member (21), the device further including a reception chamber (62) located between the ring-shaped retaining member and the needle channel, in conjunction with which, when a medium (53) that is under pressure acts upon the guiding pin (50), the switching member (22) is pressed through the retaining member (21) into the reception chamber (62), and the supporting ring (26) of the retaining member (21) supports itself against the sealing section (48) and prevents a backward movement of the switching member (22) in the direction of the piston (4) and prevents a passage of the medium (53) between the switching member (22) and the retaining member (21), even under a pressure load through the needle channel, in conjunction with which the guiding pin (50) is still guided in the guiding path (49).

32. Injection device in accordance with claim 1, characterized by the fact that the switching member (22) has a longitudinal axis which is arranged coaxial with the longitudinal axis (28) of the injection device.

33. Injection device in accordance with claim 1, characterized by the fact that the switching member (22) has a longitudinal axis which is arranged eccentric to the longitudinal axis (28) of injection device.

34. Injection device in accordance with claim 1, further comprising a pass-through channel (90) located on the surface of the switching member (22) which runs in the longitudinal direction and the pass-through channel (90) having a cross-sectional area which is smaller than a minimum cross-section for the passing through of a liquid with a viscosity that can be determined in advance.

35. Injection device in accordance with claim 1, wherein the ring-shaped retaining ring (21) includes a supporting ring (26) having an inner surface (29), the inner surface (29) of the supporting ring (26) facing the switching member (22) including an indentation that runs approximately in the longitudinal direction of the injection cylinder (2).

36. Injection device in accordance with claim 35, wherein the switching member (22) includes a surface (56) that faces the retaining member (21), and there is arranged at least one projecting part that comprises a raised part (103) that runs in the longitudinal direction of the injection cylinder (2).

* * * * *